US012702756B2

(12) United States Patent
Hansson et al.

(10) Patent No.: US 12,702,756 B2
(45) Date of Patent: Aug. 11, 2026

(54) MEDICAL FLUID SYSTEM HAVING SYSTEMS AND METHODS FOR VERIFYING VOLTAGE AND ANALOG-TO-DIGITAL CONVERTER MEASUREMENTS

(71) Applicants: Baxter International Inc., Deerfield, IL (US); Baxter Healthcare SA, Glattpark (CH)

(72) Inventors: Jimmie Marcus Axel Hansson, Limhamn (SE); Oskar Erik Frode Styrbjörn Fällman, Lund (SE); Michael Pettersson, Malmö (SE)

(73) Assignee: VANTIVE US HEALTHCARE, Deerfield, IL (US)

( * ) Notice: Subject to any disclaimer, the term of this patent is extended or adjusted under 35 U.S.C. 154(b) by 573 days.

(21) Appl. No.: 18/333,932

(22) Filed: Jun. 13, 2023

(65) Prior Publication Data

US 2023/0398297 A1 Dec. 14, 2023

Related U.S. Application Data

(60) Provisional application No. 63/352,106, filed on Jun. 14, 2022.

(51) Int. Cl.

*A61M 5/172* (2006.01)
*A61M 1/14* (2006.01)
*A61M 1/28* (2006.01)

(52) U.S. Cl.

CPC .......... *A61M 5/1723* (2013.01); *A61M 1/154* (2022.05); *A61M 1/28* (2013.01); *A61M 2205/3317* (2013.01)

(58) Field of Classification Search

CPC ...... A61M 5/1723; A61M 1/154; A61M 1/28; A61M 2205/3317; G05B 23/022

(Continued)

(56) References Cited

U.S. PATENT DOCUMENTS 9,907,908 B2 * 3/2018 Chen .................. A61M 1/1668
10,274,349 B2 * 4/2019 Nogueira ........... A61M 5/1723

(Continued)

OTHER PUBLICATIONS

International preliminary report on patentability for the European Application, EP 23741166 (Year: 2025).*

*Primary Examiner* — Christopher P McAndrew
(74) *Attorney, Agent, or Firm* — K&L Gates

(57) ABSTRACT

Systems and methods are disclosed for verifying reference voltage and analog-to-digital converter ("ADC") values during medical fluid treatment. An example system comprises a control circuit including control ADC devices associated with respective control sensors to facilitate medical fluid treatment; and a protective circuit including protective ADC devices associated with protective sensors, wherein the control circuit and the protective circuit are galvanically isolated from one another; and a computing device having a memory and a processor. The computing device may be configured to initiate a pretreatment that exposes the control sensors and the protective sensors to common pretreatment conditions (e.g., temperature and pressure); receive, during the pretreatment, control ADC values and protective ADC values; and register an error for one or both of the control circuit or the protective circuit based on a comparison of a control ADC value with a protective ADC value.

20 Claims, 8 Drawing Sheets

(58) Field of Classification Search
USPC .......................................................... 324/537
See application file for complete search history.

(56) References Cited

U.S. PATENT DOCUMENTS

2005/0101875 A1* 5/2005 Semler .................. A61B 5/282 600/509
2012/0103958 A1* 5/2012 Wallinger ................ H05B 3/58 392/468
2012/0232471 A1* 9/2012 Chen .................. A61M 1/1607 604/82
2013/0165848 A1* 6/2013 Sebesta .................... H05B 3/26 219/548
2016/0025793 A1* 1/2016 Oestreicher ............ G05B 15/00 324/538
2016/0215996 A1* 7/2016 Blair ........................ F24F 11/58
2017/0172427 A1* 6/2017 Banet ................... A61B 5/7275
2018/0177946 A1* 6/2018 Loutseiko .............. G16H 20/17
2020/0093988 A1* 3/2020 Zhong ................. A61M 5/1723

* cited by examiner 2.27%
2.27%
2.27%
ICODEXTRIN
NO
NC
CP

MEDICAL FLUID SYSTEM HAVING SYSTEMS AND METHODS FOR VERIFYING VOLTAGE AND ANALOG-TO-DIGITAL CONVERTER MEASUREMENTS

PRIORITY CLAIM AND CROSS-REFERENCE TO RELATED APPLICATION

This application claims priority to and the benefit of U.S. Provisional Patent Application No. 63/352,106, filed Jun. 14, 2022, titled MEDICAL FLUID SYSTEM HAVING SYSTEMS AND METHODS FOR VERIFYING VOLTAGE AND ANALOG-TO-DIGITAL CONVERTER MEASUREMENTS, the entire contents of which are incorporated by reference herein in their entirety and relied upon.

BACKGROUND

The present disclosure relates generally to medical fluid treatments and in particular to systems and methods for verifying voltage and analog-to-digital converter ("ADC") measurements in medical fluid treatment systems.

Due to various causes, a person's renal system can fail. Renal failure produces several physiological derangements. It is no longer possible to balance water and minerals or to excrete daily metabolic load. Toxic end products of metabolism, such as, urea, creatinine, uric acid and others, may accumulate in a patient's blood and tissue.

Reduced kidney function and, above all, kidney failure is treated with dialysis. Dialysis removes waste, toxins and excess water from the body that normal functioning kidneys would otherwise remove. Dialysis treatment for replacement of kidney functions is critical to many people because the treatment is lifesaving.

One type of kidney failure therapy is Hemodialysis ("HD"), which in general uses diffusion to remove waste products from a patient's blood. A diffusive gradient occurs across the semi-permeable dialyzer between the blood and an electrolyte solution called dialysate or dialysis fluid to cause diffusion.

Hemofiltration ("HF") is an alternative renal replacement therapy that relies on a convective transport of toxins from the patient's blood. HF is accomplished by adding substitution or replacement fluid to the extracorporeal circuit during treatment. The substitution fluid and the fluid accumulated by the patient in between treatments is ultrafiltered over the course of the HF treatment, providing a convective transport mechanism that is particularly beneficial in removing middle and large molecules.

Hemodiafiltration ("HDF") is a treatment modality that combines convective and diffusive clearances. HDF uses dialysis fluid flowing through a dialyzer, similar to standard hemodialysis, to provide diffusive clearance. In addition, substitution solution is provided directly to the extracorporeal circuit, providing convective clearance.

Most HD, HF, and HDF treatments occur in centers. A trend towards home hemodialysis ("HHD") exists today in part because HHD can be performed daily, offering therapeutic benefits over in-center hemodialysis treatments, which occur typically bi- or tri-weekly. Studies have shown that more frequent treatments remove more toxins and waste products and render less interdialytic fluid overload than a patient receiving less frequent but perhaps longer treatments. A patient receiving more frequent treatments does not experience as much of a down cycle (swings in fluids and toxins) as does an in-center patient, who has built-up two or three days' worth of toxins prior to a treatment. In certain areas, the closest dialysis center can be many miles from the patient's home, causing door-to-door treatment time to consume a large portion of the day. Treatments in centers close to the patient's home may also consume a large portion of the patient's day. HHD can take place overnight or during the day while the patient relaxes, works or is otherwise productive.

Another type of kidney failure therapy is peritoneal dialysis ("PD"), which infuses a dialysis solution, also called dialysis fluid, into a patient's peritoneal chamber via a catheter. The dialysis fluid is in contact with the peritoneal membrane in the patient's peritoneal chamber. Waste, toxins and excess water pass from the patient's bloodstream, through the capillaries in the peritoneal membrane, and into the dialysis fluid due to diffusion and osmosis, i.e., an osmotic gradient occurs across the membrane. An osmotic agent in the PD dialysis fluid provides the osmotic gradient. Used or spent dialysis fluid is drained from the patient, removing waste, toxins and excess water from the patient. This cycle is repeated, e.g., multiple times.

There are various types of peritoneal dialysis therapies, including continuous ambulatory peritoneal dialysis ("CAPD"), automated peritoneal dialysis ("APD"), tidal flow dialysis, and continuous flow peritoneal dialysis ("CFPD"). CAPD is a manual dialysis treatment. Here, the patient manually connects an implanted catheter to a drain to allow used or spent dialysis fluid to drain from the peritoneal chamber. The patient then switches fluid communication so that the patient catheter communicates with a bag of fresh dialysis fluid to infuse the fresh dialysis fluid through the catheter and into the patient. The patient disconnects the catheter from the fresh dialysis fluid bag and allows the dialysis fluid to dwell within the peritoneal chamber, wherein the transfer of waste, toxins and excess water takes place. After a dwell period, the patient repeats the manual dialysis procedure, for example, four times per day. Manual peritoneal dialysis requires a significant amount of time and effort from the patient, leaving ample room for improvement.

Automated peritoneal dialysis ("APD") is similar to CAPD in that the dialysis treatment includes drain, fill and dwell cycles. APD machines, however, perform the cycles automatically, typically while the patient sleeps. APD machines free patients from having to manually perform the treatment cycles and from having to transport supplies during the day. APD machines connect fluidly to an implanted catheter, to a source or bag of fresh dialysis fluid and to a fluid drain. APD machines pump fresh dialysis fluid from a dialysis fluid source, through the catheter and into the patient's peritoneal chamber. APD machines also allow for the dialysis fluid to dwell within the chamber and for the transfer of waste, toxins and excess water to take place. The source may include multiple liters of dialysis fluid including several solution bags.

APD machines pump used or spent dialysate from the patient's peritoneal cavity, though the catheter, to drain. As with the manual process, several drain, fill and dwell cycles occur during dialysis. A "last fill" may occur at the end of the APD treatment. The last fill fluid may remain in the peritoneal chamber of the patient until the start of the next treatment, or may be manually emptied at some point during the day.

Medical fluid systems, such as APD machines, may require a protective electrical system to provide dialysis treatment for a patient as a backup, secondary dialysis system, in the event a primary electrical system for dialysis treatment fails or performs suboptimally. The primary electrical system, known as a control system, and the protective system may be galvanically isolated from one another, but may independently coexist in the same medical device. For example, the control system and the protective system may be configured to only communicate through a serial bus. Since medical fluid systems, such as APD machines, often rely on sensors to automate dialysis processes, accurate measurements from the sensors (e.g., temperature and pressure sensors) are important to ensure that the medical fluid system is functioning properly. Such sensor measurements may be registered as voltages, and may be converted, via analog-to-digital converter ("ADC") devices, to digital signals to control fluid flow. The converted digital signals may thus rely on the accuracy and reliability of ADC values and reference voltages used by the ADC devices. However, due to the galvanic isolation between the two electrical systems (e.g., the control and the protective systems) of a medical fluid device, the reference voltages, ADC values, and digital signals based on the sensor measurements may not be accurate and/or may not be consistent.

An improved way to verify the voltage and ADC measurements in medical fluid treatment systems is needed accordingly.

SUMMARY

The present disclosure sets forth a medical fluid system, such as an automated peritoneal dialysis ("APD") system that improves patient care by verifying voltage and analog-to-digital converter ("ADC") measurements in medical fluid treatment systems, leading to a more accurate control of fluid flow and dialysis processes, and better reliance of protective systems.

In light of the disclosure set forth herein, and without limiting the disclosure in any way, in a first aspect of the present disclosure, which may be combined with any other aspect, or portion thereof, a system for verifying reference voltage and analog-to-digital converter ("ADC") values during medical fluid treatment, the system including a control circuit including a plurality of control ADC devices and a plurality of control sensors, wherein each control ADC device is associated with a respective control sensor and facilitates medical fluid treatment based on an input voltage from the respective control sensor; and a protective circuit including a plurality of protective ADC devices and a plurality of protective sensors, wherein each protective ADC device is associated with a respective protective sensor, wherein the control circuit and the protective circuit are galvanically isolated from one another; one or more processor; and a memory storing instructions that, when executed by the one or more processor, cause the system to: initiate a pretreatment for the system, wherein the pretreatment exposes the plurality of control sensors and the plurality of protective sensors to common pretreatment conditions; receive, during the pretreatment, a plurality of control ADC values corresponding to the plurality of control ADC devices, and a plurality of protective ADC values corresponding to the plurality of protective ADC devices; and register, based on a comparison of a control ADC value with a protective ADC value, an error for one or both of the control circuit or the protective circuit.

In a second aspect of the present disclosure, which may be combined with any other aspect, or portion thereof, the system includes a central processing unit ("CPU"); a first optoisolator communicatively coupling the CPU to the control circuit; and a second optoisolator communicatively coupling the CPU to the protective circuit, wherein the first and second optoisolators galvanically isolate the control circuit from the protective circuit.

In a third aspect of the present disclosure, which may be combined with any other aspect, or portion thereof, exposing the plurality of control sensors and the plurality of protective sensors to the common pretreatment conditions comprises exposing the plurality of control sensors and the plurality of protective sensors to a common temperature range or a common pressure range.

In a fourth aspect of the present disclosure, which may be combined with any other aspect, or portion thereof, the instructions, when executed, further cause the system to: determine, for each of the plurality of control ADC devices, based on the common pretreatment conditions and an expected voltage range of a respective control sensor associated with a respective control ADC device, an expected control reference voltage value of the respective control ADC device; and determine, for each of the plurality of protective ADC devices, based on the common pretreatment conditions and an expected voltage range of a respective protective sensor associated with a respective protective ADC device, an expected protective reference voltage value of the respective protective ADC device.

In a fifth aspect of the present disclosure, which may be combined with any other aspect, or portion thereof, the instructions, when executed, further cause the system to: determine, based on the plurality of control ADC values and a number of bits that the plurality of control ADC devices are configured to output, a plurality of actual control reference voltage values corresponding to the plurality of control ADC values; and determine, based on the plurality of protective ADC values and a number of bits that the plurality of protective ADC devices are configured to output, a plurality of actual protective reference voltage values corresponding to the plurality of protective ADC values.

In a sixth aspect of the present disclosure, which may be combined with any other aspect, or portion thereof, the registering of the error for one or both of the control circuit or the protective circuit is further based on one or more of: a comparison of an expected control reference voltage value of a control ADC device and an actual control reference voltage value for the control ADC device; or a comparison of an expected protective reference voltage value of a protective ADC device and an actual protective reference voltage value for the protective ADC device.

In a seventh aspect of the present disclosure, which may be combined with any other aspect, or portion thereof, the instructions, when executed, further cause the system to: determine, for each of the plurality of control ADC devices, based on the expected control reference voltage value of the respective control ADC device, an expected control input voltage value of a respective control sensor associated with the respective control ADC device; determine, for each of the plurality of control ADC devices, based on an actual control reference voltage value of the respective control ADC device, an actual control input voltage value of the respective control sensor associated with the respective control ADC device; determine, for each of the plurality of protective ADC devices, based on the expected protective reference voltage value of the respective protective ADC device, an expected protective input voltage value of a respective protective sensor associated with the respective protective ADC device; and determine, for each of the plurality of protective ADC devices, based on an actual protective reference voltage value of the respective protective ADC device, an actual protective input voltage value of the respective protective sensor associated with the respective protective ADC device; and wherein the registering of the error for one or both of the control circuit or the protective circuit is further based on one or more of: a comparison of an expected control input voltage value of a control ADC device and an actual control input voltage value for the control ADC device; or a comparison of an expected protective input voltage value of a protective ADC device and an actual protective input voltage for the protective ADC device.

In an eighth aspect of the present disclosure, which may be combined with any other aspect, or portion thereof, the plurality of control sensors comprises one or more control temperature sensor and one or more control pressure sensor, and wherein the plurality of protective sensors comprises one or more protective temperature sensor and one or more protective pressure sensor.

In a ninth aspect of the present disclosure, which may be combined with any other aspect, or portion thereof, the system includes a plurality of pumps; and a plurality of valves, wherein the plurality of pumps and the plurality of valves perform, based on the plurality of control ADC values or the plurality of protective ADC values, the medical fluid treatment.

In a tenth aspect of the present disclosure, which may be combined with any other aspect, or portion thereof, the instructions, when executed, further cause the system to determine a plurality of actual control reference voltage values corresponding to the plurality of control ADC values; determine a plurality of actual protective reference voltage values corresponding to the plurality of protective ADC values; and wherein the actual control reference voltage value and the actual protective reference voltage value, is associated with one or more of: an actual control reference voltage value of a control temperature sensor and an actual protective reference voltage value of a protective temperature sensor, respectively; or an actual control reference voltage value of a control pressure sensor and an actual protective reference voltage value of a protective pressure sensor, respectively.

In an eleventh aspect of the present disclosure, which may be combined with any other aspect, or portion thereof, the error is registered for the control circuit, and wherein the instructions, when executed, further cause the system to: disable the control circuit from facilitating the medical fluid treatment.

In a twelfth aspect of the present disclosure, which may be combined with any other aspect, or portion thereof, a method for verifying reference voltage and analog-to-digital converter ("ADC") values during medical fluid treatment, the method including initiating, by a computing device having a processor, a pretreatment for a medical fluid treatment system including a plurality of control sensors and a plurality of protective sensors, wherein the pretreatment exposes the plurality of control sensors and the plurality of protective sensors to common pretreatment conditions; receiving, by the computing device, during the pretreatment, a plurality of control ADC values corresponding to a plurality of control ADC devices associated with the respective plurality of control sensors, and a plurality of protective ADC values corresponding to a plurality of protective ADC devices associated with the respective plurality of protective sensors; and registering, by the computing device and based on a comparison of a control ADC value with a protective ADC value, an error for one or both of the control circuit or the protective circuit.

In a thirteenth aspect of the present disclosure, which may be combined with any other aspect, or portion thereof, exposing the plurality of control sensors and the plurality of protective sensors to the common pretreatment conditions comprises exposing the plurality of control sensors and the plurality of protective sensors to a common temperature range or a common pressure range.

In a fourteenth aspect of the present disclosure, which may be combined with any other aspect, or portion thereof, the method further includes determining, for each of the plurality of control ADC devices, based on the common pretreatment conditions and an expected voltage range of a respective control sensor associated with a respective control ADC device, an expected control reference voltage value of the respective control ADC device; and determining, for each of the plurality of protective ADC devices, based on the common pretreatment conditions and an expected voltage range of a respective protective sensor associated with a respective protective ADC device, an expected protective reference voltage value of the respective protective ADC device.

In a fifteenth aspect of the present disclosure, which may be combined with any other aspect, or portion thereof, the method includes determining, based on the plurality of control ADC values and a number of bits that the plurality of control ADC devices are configured to output, a plurality of actual control reference voltage values corresponding to the plurality of control ADC values; and determining, based on the plurality of protective ADC values and a number of bits that the plurality of protective ADC devices are configured to output, a plurality of actual protective reference voltage values corresponding to the plurality of protective ADC values.

In a sixteenth aspect of the present disclosure, which may be combined with any other aspect, or portion thereof, registering the error for one or both of the control circuit or the protective circuit is further based on one or more of: a comparison of an expected control reference voltage value of a control ADC device and an actual control reference voltage value for the control ADC device; or a comparison of an expected protective reference voltage value of a protective ADC device and an actual protective reference voltage value for the protective ADC device.

In a seventeenth aspect of the present disclosure, which may be combined with any other aspect, or portion thereof, the plurality of control sensors comprise one or more control temperature sensor and one or more control pressure sensor; and the plurality of protective sensors comprise one or more protective temperature sensor and one or more protective pressure sensor.

In an eighteenth aspect of the present disclosure, which may be combined with any other aspect, or portion thereof, the method includes determining a plurality of actual control reference voltage values corresponding to the plurality of control ADC values; determining a plurality of actual protective reference voltage values corresponding to the plurality of protective ADC values; and wherein the actual control reference voltage value and the actual protective reference voltage value, is associated with one or more of: an actual control reference voltage value of a control temperature sensor and an actual protective reference voltage value of a protective temperature sensor, respectively; or an actual control reference voltage value of a control pressure sensor and an actual protective reference voltage value of a protective pressure sensor, respectively.

In a nineteenth aspect of the present disclosure, which may be combined with any other aspect, or portion thereof, the error is registered for the control circuit, and further comprising: disabling the control circuit from facilitating the medical fluid treatment.

In a twentieth aspect of the present disclosure, which may be combined with any other aspect, or portion thereof, a non-transitory computer readable medium for use on a computer system containing computer-executable programming instructions for verifying voltage and analog-to-digital converter ("ADC") values during medical fluid treatment, the instructions including initiating a pretreatment for a medical fluid treatment system including a plurality of control sensors and a plurality of protective sensors, wherein the pretreatment exposes the plurality of control sensors and the plurality of protective sensors to common pretreatment conditions; receiving, during the pretreatment, a plurality of control ADC values corresponding to a plurality of control ADC devices associated with the respective plurality of control sensors, and a plurality of protective ADC values corresponding to a plurality of protective ADC devices associated with the respective plurality of protective sensors; determining, based on the predetermined conditions, a plurality of actual control reference voltage values corresponding to the plurality of control ADC values, and a plurality of actual protective reference voltage values corresponding to the plurality of protective ADC values; and registering, based on an actual control reference voltage value or an actual protective reference voltage value, and based on a comparison of a control ADC value with a protective ADC value, an error for one or both of the control circuit or the protective circuit.

In a twenty-first aspect of the present disclosure, which may be combined with any other aspect, or portion thereof, a peritoneal dialysis ("PD") system includes a PD fluid pump; a first PD fluid container for supplying PD fluid to the PD fluid pump; a second PD fluid container for supplying PD fluid to the PD fluid pump; a first reusable PD fluid line including a first connector for connecting to the first PD fluid container; and a second reusable PD fluid line including a second connector for connecting to the second PD fluid container, wherein the first and second connectors are configured to be sealingly mated together so that the first and second PD fluid lines are in fluid communication during a disinfection sequence performed between PD fluid treatments.

In a twenty-second aspect of the present disclosure, which may be combined with any other aspect, or portion thereof, the first and second connectors are sealingly mated via a threaded connection, a luer connection, or a quick-connect connector that is pushed to make a sealed connection and is pulled back to release the connection.

In a twenty-third aspect of the present disclosure, which may be combined with any other aspect, or portion thereof, the PD system further includes a third PD fluid container for supplying PD fluid to the PD fluid pump; a fourth PD fluid container for supplying PD fluid to the PD fluid pump; a third reusable PD fluid line including a third connector for connecting to the third PD fluid container; and a fourth PD fluid line including a fourth connector for connecting to the fourth PD fluid container, wherein the third and fourth connectors are configured to be sealingly mated together so that the third and fourth PD fluid lines are in fluid communication during the disinfection sequence.

In a twenty-fourth aspect of the present disclosure, which may be combined with any other aspect, or portion thereof, at least one of (i) the first and third connectors are a same type of connector or (ii) the second and fourth connectors are a same type of connector.

In a twenty-fifth aspect of the present disclosure, which may be combined with any other aspect, or portion thereof, the first and second reusable PD fluid lines are flexible.

In a twenty-sixth aspect of the present disclosure, which may be combined with any other aspect, or portion thereof, the first PD fluid container includes a second connector for connecting to the first connector of the first reusable PD fluid line, and the second PD fluid container includes a first connector for connecting to the second connector of the second reusable PD fluid line.

In a twenty-seventh aspect of the present disclosure, which may be combined with any other aspect, or portion thereof, at least one of the first and second PD fluid containers includes a "Y" or "T" type fitting having one leg leading to a first connector for connecting to the second connector of the second reusable PD fluid line and another leg leading to a second connector for connecting to the first connector of the first reusable PD fluid line.

In a twenty-eighth aspect of the present disclosure, which may be combined with any other aspect, or portion thereof, the PD system includes a pressure sensor positioned and arranged to measure a PD fluid pressure in the first and second PD fluid lines, and a control unit, the PD fluid pump under control of the control unit and the pressure sensor outputting to the control unit, the control unit configured to use the PD fluid pump and an output from the pressure sensor to perform a pressure or pressure decay test to determine whether the first and second connectors are properly mated together for the disinfection sequence.

In a twenty-ninth aspect of the present disclosure, which may be combined with any other aspect, or portion thereof, the PD system includes a clip positioned and arranged to accept the mated first and second connectors, the clip including at least one proximity sensor for detecting a presence of at least one of the first and second connectors as a condition for allowing the disinfection sequence to proceed.

In a thirtieth aspect of the present disclosure, which may be combined with any other aspect, or portion thereof, the at least one proximity sensor is a hall effect, magnetic, electromagnetic, ultrasonic, inductive, capacitive or optical sensor.

In a thirty-first aspect of the present disclosure, which may be combined with any other aspect, or portion thereof, the PD system includes first and second conductive wires located respectively along the first and second PD fluid lines, the first and second conductive wires in electrical communication with first and second conductors provided respectively by the first and second connectors, a voltage source in electrical communication with the first and second conductive wires, a current or resistance sensor in electrical communication with the first and second conductive wires, and a control unit, the current or resistance sensor outputting to the control unit, the control unit configured to analyze the sensor output to determine whether the first and second connectors are properly mated together for the disinfection sequence.

In a thirty-second aspect of the present disclosure, which may be combined with any other aspect, or portion thereof, a peritoneal dialysis ("PD") system includes a PD fluid pump; a first reusable PD fluid line for communicating PD fluid to the PD fluid pump, the first reusable PD fluid line terminating at a first connector; and a second reusable PD fluid line for communicating PD fluid to the PD fluid pump, the second reusable PD fluid line terminating at a second connector, wherein the first and second connectors are configured to be sealingly mated together so that the first and second PD fluid lines are in fluid communication during a disinfection sequence performed between PD fluid treatments.

In a thirty-third aspect of the present disclosure, which may be combined with any other aspect, or portion thereof, the first and second connectors are sealingly mated via a threaded connection, a luer connection, or a quick-connect connector that is pushed to make a sealed connection and is pulled back to release the connection.

In a thirty-fourth aspect of the present disclosure, which may be combined with any other aspect, or portion thereof, the PD system of claim 12, which further includes a third reusable PD fluid line for communicating PD fluid to the PD fluid pump, the third reusable PD fluid line terminating at a third connector; and a fourth PD fluid line for communicating PD fluid to the PD fluid pump, the fourth reusable PD fluid line terminating at a fourth connector, wherein the third and fourth connectors are configured to be sealingly mated together so that the third and fourth PD fluid lines are in fluid communication during the disinfection sequence.

In a thirty-fifth aspect of the present disclosure, which may be combined with any other aspect, or portion thereof, at least one of (i) the first and third connectors are a same type of connector or (ii) the second and fourth connectors are a same type of connector.

In a thirty-sixth aspect of the present disclosure, which may be combined with any other aspect, or portion thereof, a peritoneal dialysis ("PD") method includes providing a first reusable PD fluid line including a first connector for connecting to the first PD fluid container; providing a second reusable PD fluid line including a second connector for connecting to the second PD fluid container; and configuring the first and second connectors to be sealingly mated together so that the first and second PD fluid lines are in fluid communication during a disinfection sequence performed between PD fluid treatments.

In a thirty-seventh aspect of the present disclosure, which may be combined with any other aspect, or portion thereof, the PD method includes pumping heated disinfection through the first and second reusable PD fluid lines and the mated first and second connectors during the disinfection sequence.

In a thirty-eighth aspect of the present disclosure, which may be combined with any other aspect, or portion thereof, any of the features, functionality and alternatives described in connection with any one or more of FIGS. 1 to 8 may be combined with any of the features, functionality and alternatives described in connection with any other of FIGS. 1 to 8.

In light of the above aspects and present disclosure set forth herein, it is an advantage of the present disclosure to provide a medical fluid treatment system that has, in addition to a control circuit for controlling the flow of medical fluid in response to sensor output, a protective circuit to function as a replacement for the control circuit in the event that the control circuit registers an error.

It is another advantage of the present disclosure to provide a medical fluid treatment system that can detect errors in one or both of the control circuit or the protective circuit.

It is a further advantage of the present disclosure to provide a medical fluid treatment system that can detect errors in one or both of the control circuit or the protective circuit based on an identification of a defective ADC device in one or both of the control circuit or the protective circuit.

It is yet another advantage of the present disclosure to provide a medical fluid treatment system that can identify a defective ADC device by comparing an ADC value outputted by an ADC device of a control circuit with an ADC value outputted by a corresponding ADC device of a protective circuit.

It is yet a further advantage of the present disclosure to provide a medical fluid treatment system that can identify a defective ADC device by comparing an actual reference voltage value used by an ADC device during a known pretreatment condition with an expected reference voltage value that the ADC device would use based on the known pretreatment condition.

Moreover, it is an advantage of the present disclosure to provide a streamlined and efficient way of coupling supply and PD fluid lines together after treatment for disinfection.

Additional features and advantages are described in, and will be apparent from, the following Detailed Description and the Figures. The features and advantages described herein are not all-inclusive and, in particular, many additional features and advantages will be apparent to one of ordinary skill in the art in view of the figures and description. Also, any particular embodiment does not have to have all of the advantages listed herein and it is expressly contemplated to claim individual advantageous embodiments separately. Moreover, it should be noted that the language used in the specification has been selected principally for readability and instructional purposes, and not to limit the scope of the inventive subject matter.

DETAILED DESCRIPTION

System Overview

Figure 1:
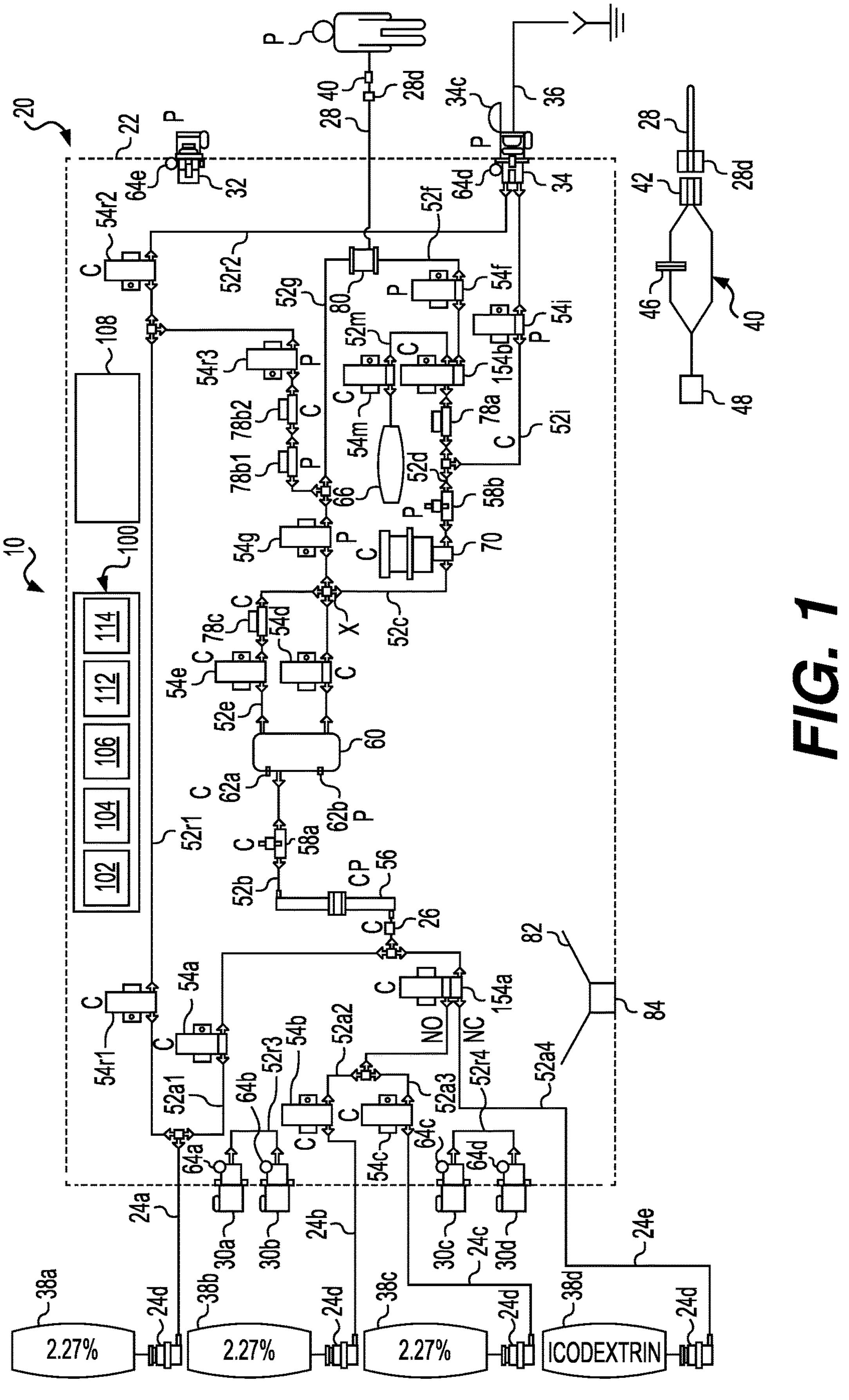
FIG. 1 is a schematic view of an example embodiment of a medical fluid system, such as a peritoneal dialysis system having structure and functionality for verifying voltage and analog-to-digital converter ("ADC") measurements in medical fluid treatment systems of the present disclosure.

Referring now to the drawings and in particular to FIG. 1, an example medical fluid system that may employ the sensor verification of a voltage reference signal of the present disclosure is illustrated by peritoneal dialysis ("PD") system 10. System 10 (also referred to as medical fluid treatment system) includes a PD machine or cycler 20 and a control unit 100 having one or more processor 102, one or more memory 104, video controller 106, a control circuit input/output controller (control I/O controller) 112, and a protective circuit input/output controller (protective I/O controller) 114. The control unit 100 may be associated with, include, or communicatively coupled with a user interface 108. Control unit 100 controls all electrical fluid flow and heating components of system 10 and receives outputs from all sensors of system System 10 in the illustrated embodiment includes durable and reusable components that contact medical fluid, such as PD fluid, which necessitates that PD machine or cycler 20 be disinfected between treatments, e.g., via heat disinfection.

System 10 in FIG. 1 includes inline dialysis fluid heater 56 located downstream from a flow switch 26 for ensuring PD fluid flow to heater 56, reusable supply lines or tubes 52*a*1 to 52*a*4 and 52*b*, air trap 60 operating with respective upper and lower level sensors 62*a* and 62*b*, air trap valve 54*d*, vent valve 54*e* located along vent line 52*e*, reusable line or tubing 52*c*, dialysis fluid pump 70, temperature sensors 58*a* and 58*b*, reusable line or tubing 52*d*, pressure sensors 78*a*, 78*b*1, 78*b*2 and 78*c*, reusable patient tubing or lines 52*f* and 52*g* having respective valves 54*f* and 54*g*, dual lumen reusable patient line 28, hose reel 110 for retracting patient line 28, reusable drain tubing or line 52*i* extending to drain line connector 34 and having a drain line valve 54*i*, and reusable recirculation disinfection tubing or lines 52*r*1 and 52*r*2 operating with respective disinfection valves 54*r*1 and 54*r*2. A third recirculation or disinfection tubing or line 52*r*3 extends between disinfection connectors 30*a* and 30*b* for use during disinfection. A fourth recirculation or disinfection tubing or line 52*r*4 extends between disinfection connectors 30*c* and 30*d* for use during disinfection.

System 10 further includes PD fluid containers or bags 38*a* to 38*c* (e.g., holding the same or different formulations of PD fluid), which connect to distal ends 24*d* of reusable PD fluid lines 24*a* to 24*c*, respectively. System 10*d* further includes a fourth PD fluid container or bag 38*d* that connects to a distal end 24*d* of reusable PD fluid line 24*e*. Fourth PD fluid container or bag 38*d* may hold the same or different (e.g., icodextrin) type of PD fluid than provided in PD fluid containers or bags 38*a* to 38*c*. Reusable PD fluid lines 24*a* to 24*c* and 24*e* extend in one embodiment through apertures (not illustrated) defined or provided by housing 22 of cycler 20.

System 10 in the illustrated embodiment includes four disinfection connectors 30*a* to 30*d* for connecting to distal ends 24*d* of reusable PD fluid lines 24*a* to 24*c* and 24*e*, respectively, during disinfection. System 10 also provides patient line connector 32 that includes an internal lumen, e.g., a U-shaped lumen, which directs fresh or used dialysis fluid from one PD fluid lumen of dual lumen reusable patient line 28 into the other PD fluid lumen. Reusable supply tubing or lines 52*a*1 to 52*a*4 communicate with reusable supply lines 24*a* to 24*c* and 24*e*, respectively. Reusable supply tubing or lines 52*a*1 to 52*a*3 operate with valves 54*a* to 54*c*, respectively, to allow PD fluid from a desired PD fluid container or bag 38*a* to 38*c* to be pulled into cycler 20. Three-way valve 154*a* in the illustrated example allows for control unit 100 to select between (i) 2.27% glucose dialysis fluid from container or bag 38*b* or 38*c* and (ii) icodextrin from container or bag 38*d*. In the illustrated embodiment, icodextrin from container or bag 38*d* is connected to the normally closed port of three-way valve 154*a*.

FIG. 1 also illustrates that system 10 includes and uses disposable filter set 40, which communicates fluidly with the fresh and used PD fluid lumens of dual lumen reusable patient line 28. Disposable filter set 40 includes a disposable connector 42 that connects to distal end 28*d* of reusable patient line 28. Disposable filter set 40 includes a connector 48 that connects to the patient's transfer set. Disposable filter set 40 further includes a sterilizing grade filter membrane 46 that further filters fresh PD fluid.

System 10 is constructed in one embodiment such that drain line 52*i* during filling is fluidly connected downstream from dialysis fluid pump 70. In this manner, if drain valve 54*i* fails or somehow leaks during a patient fill, fresh PD fluid is pushed down disposable drain line 36 instead of used PD fluid potentially being pulled into pump 70. Disposable drain line 36 is in one embodiment removed for disinfection, while drain line connector 34 is capped via a cap 34*c*.

System 10 further includes a leak detection pan 82 located at the bottom of housing 22 of cycler 20 and a corresponding leak detection sensor 84 outputting to control unit 100. In the illustrated example, system 10 is provided with an additional pressure sensor 78*c* located upstream of dialysis fluid pump 70, which allows for the measurement of the suction pressure of pump 70 to help control unit 100 to more accurately determine pump volume. Additional pressure sensor 78*c* in the illustrated embodiment is located along vent line 52*e*, which may be filled with air or a mixture of air and PD fluid, but which should nevertheless be at the same negative pressure as PD fluid located within PD fluid line 52*c*.

System 10 in the example of FIG. 1 includes redundant pressure sensors 78*b*1 and 78*b*2, the output of one of which is used for pump control, as discussed herein, while the output of the other pressure sensor is a safety or watchdog output to make sure the control pressure sensor is reading accurately. Pressure sensors 78*b*1 and 78*b*2 are located along a line including a third recirculation valve 54*r*3. In still a further example, system 10 may employ one or more cross, marked via an X in FIG. 1, which may (i) reduce the overall amount and volume of the internal, reusable tubing, (ii) reduce the number of valves needed, and (iii) allow the portion of the fluid circuitry shared by both fresh and used PD fluid to be minimized.

System 10 in the example of FIG. 1 further includes a source of acid, such as a citric acid container or bag 66. Citric acid container or bag 66 is in selective fluid communication with second three-way valve 154*b* via a citric acid valve 54*m* located along a citric acid line 52*m*. Citric acid line 52*m* is connected in one embodiment to the normally closed port of second three-way valve 154*b*, so as to provide redundant valves between citric acid container or bag 66 and the PD fluid circuit during treatment. The redundant valves ensure that no citric (or other) acid reaches the treatment fluid lines during treatment. Citric (or other) acid is instead used during disinfection.

It should be appreciated that system 10 is not required to (i) be a PD system, or (ii) use redundant or durable components that are disinfected between uses to employ the sensor verification of a voltage reference signal of the present disclosure. System 10 may instead be any type of medical fluid system and may employ a disposable set having a disposable pumping portion that contacts the corresponding medical fluid. System 10 will however have components that are used for the control of treatment, which are marked with a "C" in FIG. 1 and components that are used for safety or backup as protective components, which are marked with a "P" in FIG. 1.

Verifying Reference Voltage and ADC Values

Figure 2:
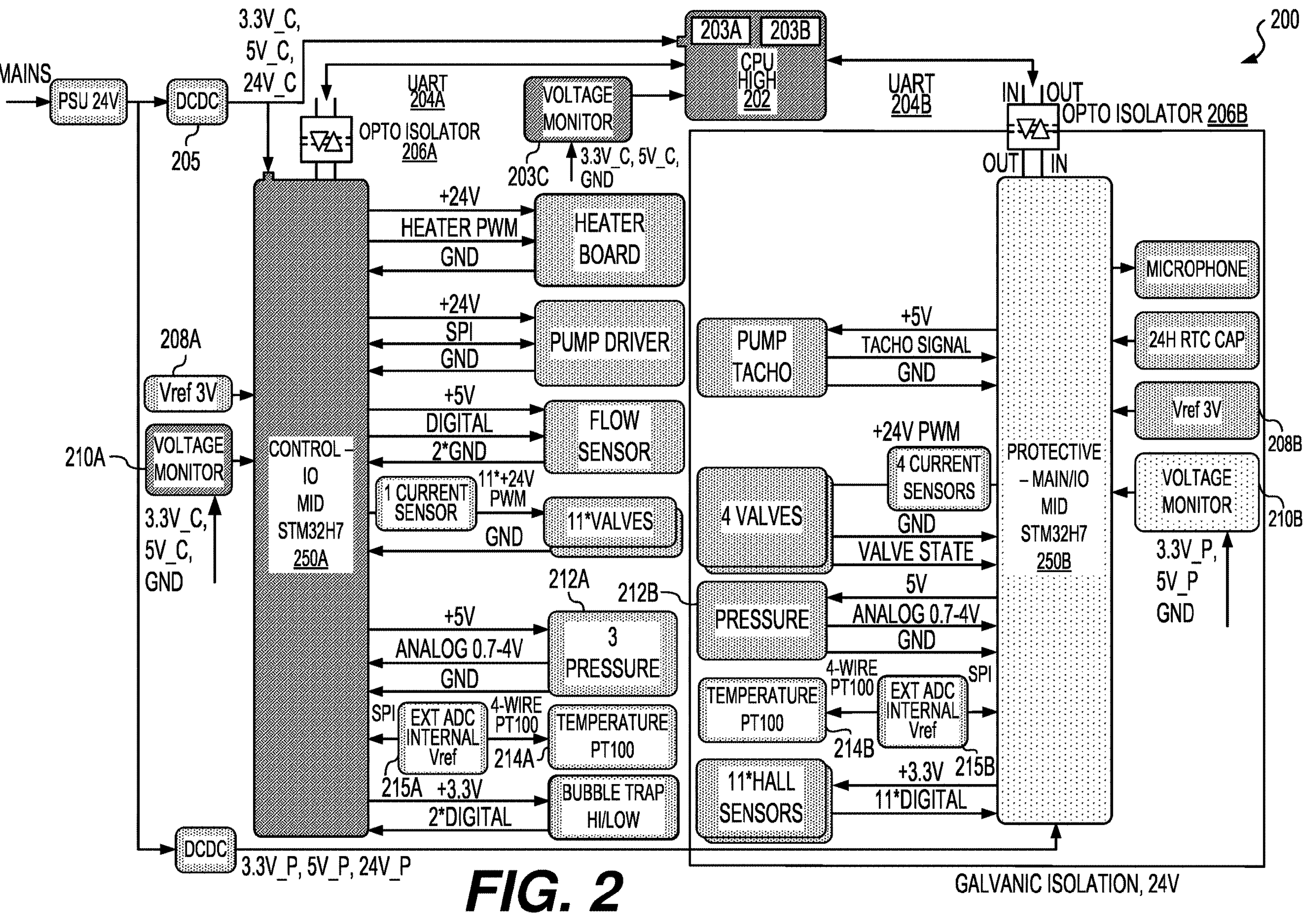
FIG. 2 is an electronic block diagram of a system for verifying voltage and ADC measurements for a medical fluid treatment system, according to an example embodiment of the present disclosure.

FIG. 2 is an electronics block diagram of a system 200 for verifying voltage and ADC measurements for a medical fluid treatment system, according to an example embodiment of the present disclosure. As shown in FIG. 2, the system may include a CPU 202, a control input/output (I/O) circuit 250A, and a protective main I/O circuit 250B. Each of the components of the system may be powered by a power supply, whose voltage may be monitored. For example, voltage monitor 203A may monitor voltage of rails directing power to the CPU 202, voltage monitor 210A may monitor voltage of rails directing power to the control I/O circuit 250A, and voltage monitor 210B may monitor voltage of rails directing power to the protective main I/O circuit 250B. In at least one embodiment, voltage rails directing power to the CPU 202 may be shared with the voltage rails directing power to the control I/O circuit 250A.

The CPU 202 may include, and/or form a part of, control unit 100, as previously described in relation to FIG. 1, and may include, comprise, or share one or more component and/or function of control unit 100. For example, the CPU 202 may include a processor 203A and memory 203B (e.g., as in processor 102 and memory 104 of control unit 100). The processor 203A may include any one or more type of digital circuit configured to perform operations on a data stream, including functions described in the present disclosure. The memory 203B may include any type of long term, short term, volatile, nonvolatile, or other memory and is not to be limited to any particular type of memory or number of memories, or type of media upon which memory is stored. The memory may store instructions that, when executed by the processor 203A, can cause the CPU 202 and/or the system 200 to perform one or more step, method, or process discussed herein. The CPU 202 may further employ a serial bus (e.g., universal asynchronous receiver-transmitters ("UART") 204A and 204B) to communicate with the control I/O circuit 250A and the protective main I/O circuit 250B (e.g., via optoisolators 206A and 206B, respectively).

The control input/output (I/O) circuit 250A and the protective main I/O circuit 250B, also referred to herein as control circuit and protective circuit, respectively, may be galvanically isolated. The galvanic isolation may prevent current flow between the control circuit 250A and the protective circuit 250B, and may ensure that the system 200 is "single fault safe". For example, if the two control circuit 250A and the protective circuit 250B are not galvanically isolated, a single fault in the control DCDC converter 205 may put 24V on the 3.3V rail. This may destroy components of the control and protective circuits and may place the medical fluid treatment system in an unknown state. However, the galvanic isolation creates a barrier between the two circuits such that, in the above-mentioned scenario, only the control circuit would go into the unknown state. The protective circuit would detect such a fault of the control circuit thorough the serial communication bus (e.g., UART 204B) and would put the medical fluid treatment system in a safer state (e.g., by replacing the control circuit as the active circuit).

As shown in FIG. 2, the control circuit 250A and the protective circuit 250B may be communicatively coupled to the CPU 202 via optoisolators 206A and 206B. The optoisolator 206A and 206B may be used to maintain the galvanic isolation between the control circuit from the protective circuit. The optoisolators 206A and 206B may allow the control unit 100 (e.g., CPU 202) to turn off the Control I/O circuit 250A node when the system 200 is in a standby mode. The presence of the optoisolators 206A and 206B on the UART buses 204A and 204B, respectively, may thus eliminate and/or reduce the potential risk if the control unit 100 (e.g., CPU 202) were to inadvertently feed voltage (e.g., 3.3 V) to pins of the control I/O circuit 250A and/or protective I/O circuit 250B and harm the system 200 while the system is unpowered and/or in a standby mode.

The control circuit 250A and protective circuit may each include a plurality of sensors to measure conditions (e.g., pressure and temperature) in the medical fluid treatment system. For example, as shown in FIG. 2, the control circuit may include three pressure sensors 212*a* and a temperature sensor 214A. The protective circuit may include pressure sensor 212B and temperature sensor 214B. The sensors outputs may include input voltages that relate to the measured entity (e.g., pressure or sensor). The input voltage may be received by an ADC device associated with the sensor. The ADC device may translate analog signals provided by the sensor (e.g., input voltage) to digital signals (e.g., ADC values) that may be used by the system 200 to control medical fluid flow. For example, as shown in FIG. 2, ADC device 215A may receive the sensor outputs from temperature sensor 214A of the control circuit 250A, and ADC device 215B may receive the sensor outputs from temperature sensor 214B of the protective circuit 250B. In some embodiments, ADC devices 215A and 215B may also translate analog signals received by pressure sensors 212A and 212B, respectively. Alternatively, ADC devices used to translate analog signals received from pressure sensors 212A and 212B may be separate (e.g., distinguishable) from the ADC devices used to translate analog signals received from temperature sensors 214A and 214B. For ease of explanation, as used herein, ADC device 215A may refer to any ADC device used to translate analog signals from sensors in the control circuit 250A, and ADC device 215B may refer to any ADC device used to translate analog signals from sensors in the protective circuit 250B. The ADC device may also use a reference voltage when translating the analog signal from the sensor to the digital signal. In some aspects, the reference voltage may relate to a range or ceiling of input voltage values received by an ADC device. For example, as shown in FIG. 2, based on the voltage values received by voltage monitors 210A and 210B, a reference voltage 208A and 208B may for example, be 3 VDC.

The protective circuit 250B may, like the control circuit 250A, include sensors and their corresponding ADC devices for receiving sensor output from their respective sensors. Moreover, the protective circuit 250B may serve as a secondary circuit or system to ensure that the patient is kept safe if the control circuit 250A fails. Thus, the protective circuit 250B may include various sensors and their respective ADC devices that are cognates of (e.g., correspond to the same locations where conditions are measured in the medical fluid treatment system) various sensors and respective ADC devices in the control circuit 250A. For example, the control circuit 250A and protective circuit 250B may each have their own temperature and pressure sensors to ensure that dialysis fluid sent to the patient is maintained within a safe pressure and temperature range. The sensors generate analog signals (e.g., voltages) that the ADC devices convert to a digital value (e.g., ADC value) used for pump and heater regulation in the medical fluid treatment system. To know if the analog to digital value conversion is correct, a known voltage reference value must be used on both the control and protective system, as will be discussed herein.

Figure 3:
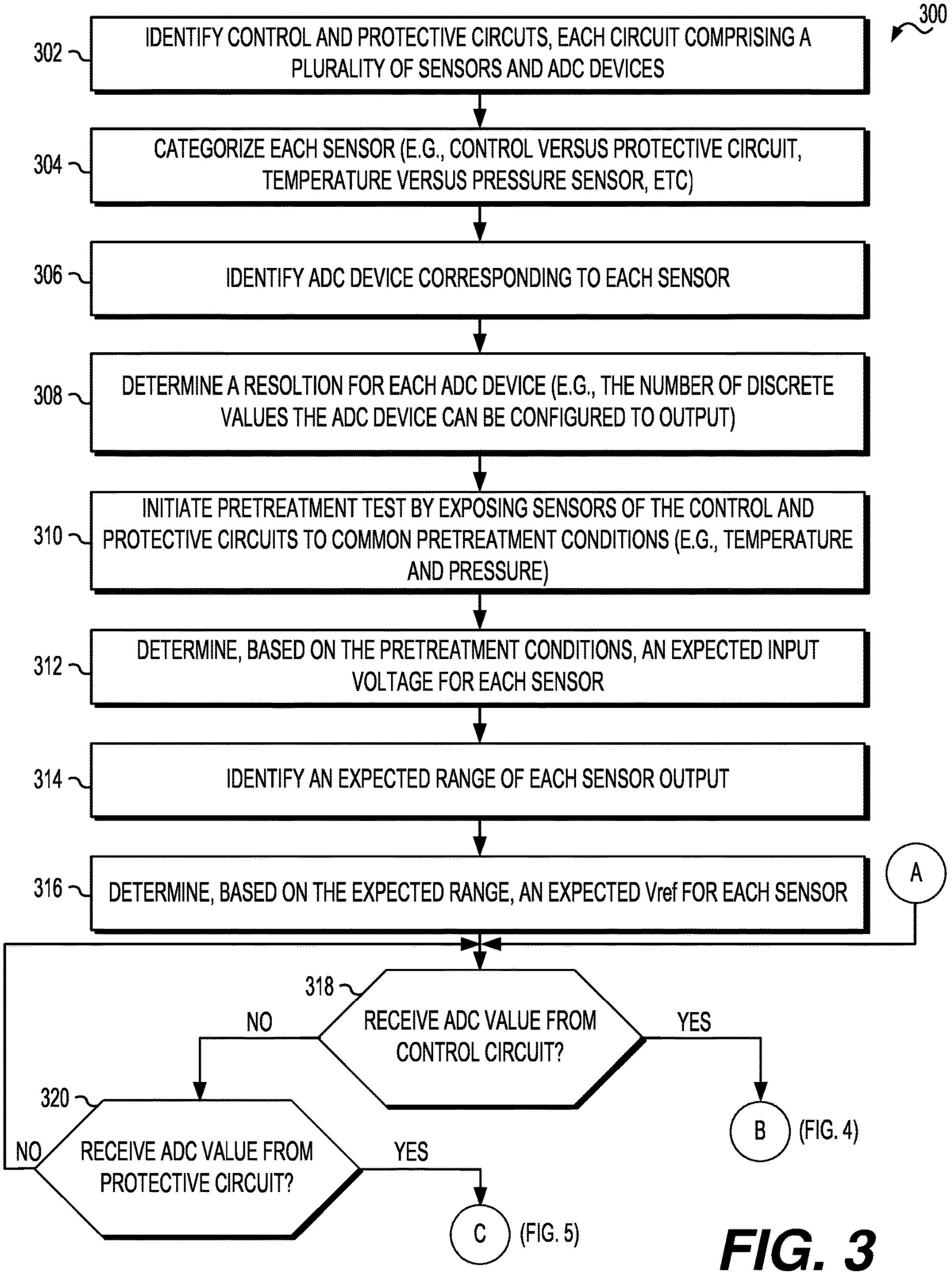
FIG. 3 is a process flow diagram of an example process for verifying voltage and ADC measurements for a medical fluid treatment system, according to an example embodiment of the present disclosure.

FIG. 3 is a process flow diagram of an example process 300 for verifying voltage and ADC measurements for a medical fluid treatment system 10, according to an example embodiment of the present disclosure. Process 300 may be performed by a processor (e.g., processor 102 of control unit 100 and/or processor 203A of CPU 202). The processor 102/203A may rely on instructions stored in memory (e.g., memory 104 of control unit 100 and/or memory 203B of CPU 202). For simplicity, "computing device" may be used to refer to the control unit 100 and/or CPU 202. In some embodiments, one or more steps may be performed by, or may involve subsequent steps caused to be performed by, the control circuit 250A or the protective circuit 250B. Such steps may be indicated herein.

In order to verify voltage and ADC measurements for the medical fluid treatment system 10, process 300 may begin with the computing device 100/202 (e.g., the CPU 202 or control unit 100) identifying and assessing the components of the medical fluid treatment system 10 that is managed by the computing device 100/202. Such steps (e.g., blocks 302-308) may occur, for example, at start-up. For example, at block 302, computing device 100/202 may identify the control circuit 250A and protective circuit 250B. As discussed previously, in relation to FIG. 2, each circuit (e.g., control circuit 250A or protective circuit 250B) may include a plurality of sensors and ADC devices. The computing device 100/202 may categorize each sensor (block 304). For example, the computing device 100/202 may detect and identify each sensor as belonging to either the control circuit 250A or the protective circuit 250B, and may detect and identify each sensor by its type (e.g., a temperature sensor or a pressure sensor). In some aspects, the identified sensors may be categorized further (e.g., by a location on the medical fluid treatment system that the sensor gages, a valve or pump associated with the sensor, etc.).

As discussed previously, the medical fluid treatment system 10 includes ADC devices 215A, 215B that convert analog signals received by the sensors to digital signals that may be used to effect control of various mechanisms (e.g., valves, pumps, etc.) of the medical fluid treatment system 10. Such analog signals (e.g., input voltages) received by the ADC devices 215A, 215B from the sensors that correlate to a detected physical phenomenon (e.g., temperature, pressure, etc.). Each sensor may thus be associated with an ADC device 215A/215B, such that a sensor output (e.g., the input voltage) from a given sensor is designated to be sent to and received by the ADC device 215A/215B (e.g., via a conductor). Thus, at block 306, the computing device 100/202 may identify the ADC device 215A/215B corresponding to each sensor. The conversion of analog signals (e.g., input voltage) to digital signals (e.g., ADC values) by each ADC device 215A/215B may be affected by characteristics or configurations of the ADC device itself. For example, a resolution of the ADC device 215A/215B may indicate the number of different (e.g., discrete) values the ADC device 215A/215B can produce over an allowed range of analog input values. The number of discrete values available for the ADC device 215A/215B to produce is usually a power of two. If an ADC device 215A/215B is configured to have a resolution of n bits (e.g., an n-bit ADC device), the number of discrete digital levels that can be produced by the ADC device may be $2^n$. For example, an 8-bit ADC device with a resolution of 8 bits can encode an analog input to one in 256 different levels ($2^8=256$). Thus, at block 308, the computing device 100/202 may identify or determine a resolution of each ADC device 215A/215B (e.g., the number of discrete values the ADC device 215A/215B is configured to output).

Process 300 may include preparing for and performing a pretreatment test. The pretreatment test, as described herein, may expose sensors in both the control circuit 250A and the protective circuit 250B to a common, predetermined range of physical conditions (e.g., a shared temperature or temperature range, and a shared pressure or pressure range). As used herein, sensors and their corresponding ADC devices in the control circuit 250A may be referred to as control sensors (212A and 214A) and control ADC devices 215A, respectively; sensors and their corresponding ADC devices in the protective circuit may be referred to as protective sensors (212B and 214B) and protective ADC devices 215B, respectively. Thus, at block 310, the computing device 100/202 may expose the plurality of control sensors (212A and 214A) and the plurality of protective sensors (212B and 214B) to common pretreatment conditions (e.g., a shared temperature or temperature range and a shared pressure or pressure range).

In some embodiments, each sensor of a given circuit (e.g., a control circuit 250A or protective circuit 250B) may be used to gauge a specific location in the medical fluid treatment system 10. Since the protective circuit 250B can serve as a backup circuit of the medical fluid treatment system 10 to service a patient when a control circuit 250A fails, it is expected that each location in which a control sensor 212A/214A is situated may also have a corresponding protective sensor 212B/214B. For example, a specific pump in a medical fluid treatment system may be associated with a control pressure sensor 212A and a protective pressure sensor 212B. As another example, a specific valve in the medical fluid treatment system 10 may be associated with a control temperature sensor 214A and a protective temperature sensor 214B. Thus, one or more control sensors (212A and 214A) of the control circuit 250A may have corresponding protective sensors (212B and 214B) of the protective circuit 250B (e.g., for one or more location within the medical fluid treatment system 10).

In some embodiments, exposing the plurality of control sensors (212A and 214A) and the plurality of protective sensors (212B and 214B) to common pretreatment conditions may involve exposing the corresponding control sensor 212A/214A and protective sensor 212B/214B of each location in the medical fluid treatment system 10 to the same pretreatment conditions. However, the pretreatment conditions (e.g., a pressure range, a temperature range, etc.) may vary from location to location.

The pretreatment test may be performed prior to use of the medical fluid treatment system 10 to service a patient, e.g., so that the detection of any defective circuits and/or defective components may preempt the use of the defective circuit and/or defective components.

At block 312, the computing device 100/202 may determine, based on the pretreatment conditions, an expected input voltage for each sensor. As previously discussed, the control circuit 250A and the protective circuit 250B are galvanically isolated, while the computing device 100/202 is communicatively coupled to the two circuits via optoisolators 206A, 206B to maintain the galavanic isolation between the two circuits. Thus, the computing device (e.g., control unit 100 and/or CPU 202) may not be able to directly measure an input voltage received by a control sensor 212A/214A or a protective sensor 212B/214B, as doing so may interrupt the galvanic isolation and cause damage. Thus, the control circuit 250A may need to estimate the expected input voltage based on the pretreatment condition. For example, the computing device 100/202 may rely on lookup tables (e.g., stored in memory 104 and/or 203B) that link temperature values to voltage values, or link pressure values to voltage values. In some embodiments, the linkages may be based on a linear or nonlinear relation. The computing device 100/202 may rely on its knowledge of the pretreatment conditions (e.g., the temperatures or pressures that sensors are exposed to) to determine the expected input voltage of each sensor in the control and protective circuits 250A, 250B.

At block 314, the computing device 100/202 may identify an expected range of each sensor output. The expected range may be a range of voltage signals that a given sensor is able to output. Such range of voltage signals may be coextensive with, or may surpass the range of voltage input signals that a sensor is expected to product based on a range of a pretreatment condition (e.g., pressure range, temperature range, etc.). In some aspects, the expected range of each sensor output may be the possible range of analog signals the sensor may be configured to output, irrespective of the conditions or current output. In other aspects, the expected range of each sensor output identified in block 314 may be based on the pretreatment conditions.

At block 316, the computing device 100/202 may determine, based on the expected range, an expected reference voltage, Vref, for each sensor. The reference voltage may refer to a maximum voltage level that an ADC device can convert (e.g., the ceiling of what the ADC device 215A/215B can convert). The reference voltage may be used as a yardstick against which input voltage may be measured. In one embodiment, the reference voltage may be the upper end of the expected range identified in block 314. In some embodiments, the input voltage, reference voltage, digital signal outputted by an ADC device 215A/215B (ADC value), and a resolution of the ADC device ($2^n$) may be related as:

$$Vin = ADC\frac{Vref}{2^n},$$

where Vin is the input voltage received by the ADC device (from its associated sensor), ADC is the ADC value outputted by the ADC device, Vref is the reference voltage associated with the sensor, and $2^n$ refers to the number of discrete values that the ADC device 215A/215B is configured to output (e.g., a resolution of the ADC device). The above described relation may be used to determine actual input voltage values of each sensor, as will be described herein, after the ADC values are received by the computing device.

As previously discussed, the medical fluid treatment system 10 can be subjected to the pretreatment test by exposing the control sensors and protective sensors to the pretreatment conditions (e.g., a common set of predetermined temperatures and pressures). The control sensors and protective sensors may thus generate input voltages indicative of, or intended to be indicative of, the pretreatment conditions. The ADC devices (215A and 215B) associated with the control sensors and protective sensors may thus receive these input voltages.

As part of managing the medical fluid treatment system 10, the computing device 100/202 may routinely monitor to see if ADC values have been generated by ADC devices 215A/215B of the control circuit 250A or the protective circuit 250B. Such ADC values may be sent to the computing device 100/202 by the ADC devices (e.g., via the UART 204A and 204B). For example, the computing device 100/202 may determine whether it has received an ADC value (e.g., from an ADC device) from the control circuit 250A (block 318). If so, the computing device 100/202 may proceed to perform process 400 described in FIG. 4. The computing device 100/202 may also determine whether it has received an ADC value (e.g., from an ADC device 215A/215B) from the protective circuit 250B (block 320). If so, the computing device 100/202 may proceed to perform process 500 described in FIG. 5.

Figure 4:
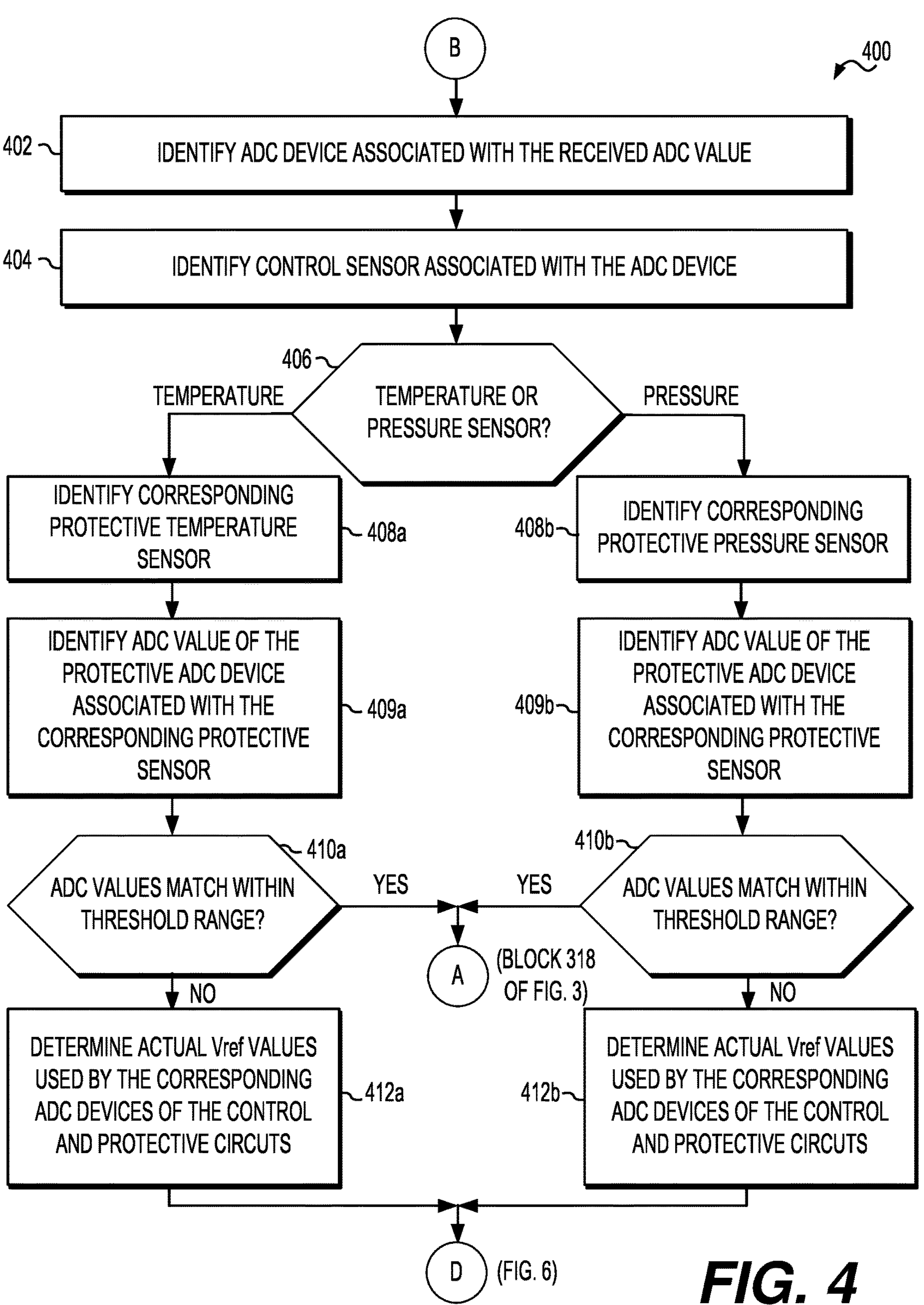
FIG. 4 is a process flow diagram of an example process for verifying voltage and ADC measurements obtained by a control circuit of a medical fluid treatment system, according to an example embodiment of the present disclosure.

FIG. 4 is a process flow diagram of an example process 400 for verifying voltage and ADC measurements obtained by a control circuit 250A of a medical fluid treatment system 10 according to an example embodiment of the present disclosure. As previously discussed, process 400 may be performed by the computing device 100/202 during the pretreatment test after the computing device 100/202 has received an ADC value from the control circuit 250A.

Referring to process 400, the computing device 100/202 may identify the ADC device associated with the received ADC value (block 402), and may identify the control sensor 212A/214A associated with the identified ADC device (block 404). At block 406, the computing device 100/202 may identify whether the control sensor is a temperature sensor 214A or a pressure sensor 212A.

As previously discussed, control sensors (212A and 214A) and protective sensors (212B and 214B) may be situated in, or positioned, to measure physical phenomena at common locations in the medical fluid treatment system 10. For example, a specific pump in the medical fluid treatment system 10 may be associated with a control pressure sensor 212A and a protective pressure sensor 212B. If the control pressure sensor 212A and/or its associated ADC device 215A is found to be defective at identifying the pressure at the specific pump, the medical fluid treatment system may then rely on the protective pressure sensor 212B and its associated ADC device 215B for the pressure measurement and identification. In another example, a specific valve in the medical fluid treatment system 10 may be associated with a control temperature sensor 214A and a protective temperature sensor 214B. If the control temperature sensor 214A and/or its associated ADC device 215A is found to be defective at identifying the temperature of a fluid at the specific valve, the medical fluid treatment system 10 may then rely on the protective temperature sensor 214B and its associated ADC device 215B for the temperature measurement and identification. Thus, a control sensor 212A/214A of the control circuit 250A may have a corresponding protective sensor 212B/214B in the protective circuit 250B (e.g., based on a location within the medical fluid treatment system 10).

Consequently, if the control sensor is a temperature sensor 214A (referred to herein as control temperature sensor), the computing device 100/202 may identify a corresponding temperature sensor 214B in the protective circuit (referred to herein as protective temperature sensor) (block 408A). The computing device 100/202 may identify the ADC device 215B associated with the corresponding protective temperature sensor 214B (referred to herein as the protective ADC device associated with the protective pressure sensor), and may determine the corresponding ADC value received from that protective ADC device 215B (block 409A).

At block 410A, the computing device 100/202 may determine whether the ADC values match within a threshold range. The ADC values being compared at bock 410A are the ADC value received from the ADC device 215A of the control circuit 250A and the ADC value received from the corresponding protective ADC device 215B of the protective circuit 250B. The threshold range may be a predetermined tolerance level to identify whether the two ADC values satisfy a similarity or matching threshold. The threshold range may be adjusted, e.g., by an operator of the medical fluid treatment system 10. If there is a match, the computing device 100/202 may deem that the ADC devices (control ADC device 215A and the protective ADC device 215B), from which the ADC values are received, are not defective. The computing device 100/202 may continue to monitor to see if there are additional ADC values received from the control circuit 250A (block 318 as previously described in relation to FIG. 3). Also or alternatively, the computing device 100/202 may deem, based on the match, that the two ADC devices (the control ADC device 215A of the control temperature sensor 214A and the protective ADC device 215B of the corresponding protective temperature sensor 214B) perform similarly enough. In such cases, it may be possible, for example, that any defect in one of the two ADC devices is countered by a defect to the same degree in the other of the two ADC devices, thus negating the detrimental effect of the defect. As will be described further in connection with FIG. 6, the computing device 100/202 may compare the ADC value outputted by its shared voltage rails (e.g., 3.3V and 5V) with the ADC values from the control and/or protective circuits 250A, 250B. By using a third ADC value (e.g., from the shared voltage rail surrounding the computing device 100/202 itself), an additional layer of check may be provided to confirm that the ADC values are reasonable.

If, at block 410A, the ADC values do not match, the computing device 100/202 may determine the actual reference voltage values used by the corresponding ADC devices of the control and protective circuits 250A, 250B. As explained previously, the relationship between reference voltage, input voltage, ADC value, and a resolution of an ADC device 215A/215B may be summarized as:

$$Vin = ADC\frac{Vref}{2^n},$$

where Vin is the input voltage received by the ADC device (from its associated sensor), ADC is the ADC value outputted by the ADC device, Vref is the reference voltage associated with the sensor, and $2^n$ refers to the number of discrete values the ADC device is configured to output (e.g., a resolution of the ADC device). Since the resolution ($2^n$) of the ADC device is determined in block 308, the expected input voltage is estimated based on pretreatment conditions in block 312, and the ADC value (ADC) is received from the control ADC device 215A in block 318, the actual reference voltage ($Vref_{actual}$) may be computed as:

$$Vref_{actual} = 2^n\frac{Vin}{ADC}.$$

Moreover, the actual reference voltage of an ADC device may be different from the expected reference voltage value of the ADC device that was computed in block 316. For example, a defective ADC device may yield an actual reference voltage that is different from the expected reference voltage. Thus, at block 412A, the computing device 100/202 determines the actual reference voltage values used by the ADC devices (215A and 215B) associated with the corresponding temperature sensors of the control and protective circuits 250A, 250B (ADC device 215A associated with the control temperature sensor 214A and the ADC device 215B associated with the protective temperature sensor 214B).

Figure 6:
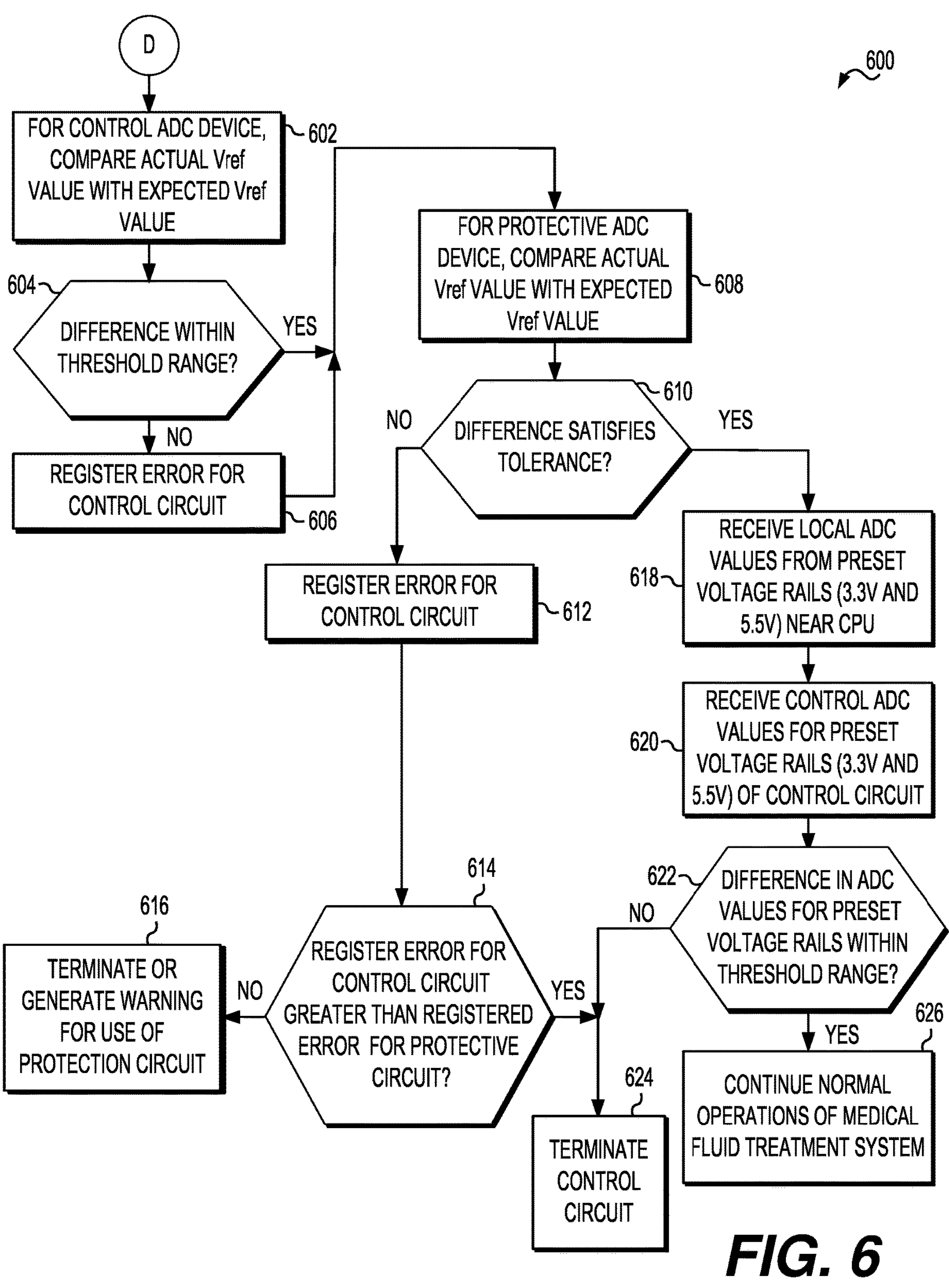
FIG. 6 is a process flow diagram of an example process for assessing fault based on voltage and ADC measurements in a medical fluid treatment system, according to an example embodiment of the present disclosure.

Process 400 may proceed to process 600 shown in FIG. 6 (as indicated by label "D" in FIGS. 4 and 6. As will be described further below, in process 600, the computing device 100/202 may use the actual ADC values and actual reference voltage values to determine which ADC device, the control ADC device 215A or the protective ADC device 215B, is at fault.

If, at block 406, the computing device 100/202 determines that the control sensor associated with the ADC device 215A is a pressure sensor 212A (control pressure sensor), the computing device 100/202 may proceed through blocks 408B, 409B, 410B, and 412B, which may share one or more step or characteristic as the previously discussed blocks 408A, 409A, 410A, and 412A.

For example, the computing device 100/202 may identify a corresponding pressure sensor 212B in the protective circuit 250B (referred to herein as protective pressure sensor) (block 408B). The computing device may identify the ADC device 215B associated with the corresponding protective pressure sensor 212B (referred to herein as the protective ADC device associated with the protective pressure sensor), and may determine the corresponding ADC value received from that protective ADC device 215B (block 409B).

At block 410B, the computing device 100/202 may determine whether the ADC values match within a threshold range. The ADC values being compared are the ADC value received from the ADC device 215A of the control circuit 250A and the ADC value received from the corresponding protective ADC device 215B of the protective circuit 250B. The threshold range may be a predetermined tolerance level used to identify whether the two ADC values satisfy a similarity or matching threshold. The threshold range may be adjusted, e.g., by an operator of the medical fluid treatment system 10. If there is a match, the computing device 100/202 may deem that the ADC devices (control ADC device 215A and the protective ADC device 215B), from which the ADC values are received, are not defective. The computing device 100/202 may continue monitoring to see if there are additional ADC values received from the control circuit 250A (block 318 as previously described in relation to FIG. 3). Also or alternatively, the computing device 100/202 may deem, based on the match, that the two ADC devices (215A and 215B) perform similarly enough. For example, it may be possible that any defect in one of the two ADC devices is countered by a defect to the same degree in the other of the two ADC devices, thus negating the detrimental effect of the defect. As will be described further in connection with FIG. 6, the computing device 100/202 may compare the ADC value outputted by its shared voltage rails (e.g., 3.3V and 5V) with the ADC values from the control and/or protective circuits 250A, 250B. By using a third ADC value (e.g., from the shared voltage rail surrounding the computing device 100/202 itself), an additional layer of check may be provided to confirm that the ADC values are reasonable.

If, at block 410B, the ADC values do not match, the computing device 100/202 may determine the actual reference voltage values used by the corresponding ADC devices of the control and protective circuits 250A, 250B. As explained previously, the relationship between reference voltage, input voltage, ADC value, and a resolution of an ADC device may be summarized as:

$$Vin = ADC\frac{Vref}{2^n},$$

where Vin is the input voltage received by the ADC device (from its associated sensor), ADC is the ADC value outputted by the ADC device, Vref is the reference voltage associated with the sensor, and $2^n$ refers to the number of discrete values the ADC is configured to output (e.g., a resolution of the ADC device). Since the resolution ($2^n$) of the ADC device is determined in block 308, the expected input voltage is estimated based on pretreatment conditions in block 312, and the ADC value (ADC) is received from the control ADC device 215A in block 318, the actual reference voltage ($Vref_{actual}$) may be computed as:

$$Vref_{actual} = 2^n\frac{Vin}{ADC}.$$

Moreover, the actual reference voltage of an ADC device may be different from the expected reference voltage value of the ADC device that is computed in block 316. For example, a defective ADC device may yield an actual reference voltage that is different from the expected reference voltage. Thus, at block 412B, the computing device 100/202 determines the actual reference voltage values used by the ADC devices associated with the corresponding pressure sensors of the control and protective circuits (ADC device 215A associated with the control pressure sensor 212A and the ADC device 215B associated with the protective pressure sensor 212B).

Process 400 may proceed to process 600 shown in FIG. 6 (as indicated by label "D" in FIGS. 4 and 6. As will be described further below, in process 600, the computing device 100/202 may use the actual ADC values and actual reference voltage values to determine which ADC device, the control ADC device 215A or the protective ADC device 215B, is at fault. In some embodiments, if the computing device 100/202 determines that the control circuit 250A is at fault as a result of the defective ADC device 215A (e.g., due to a difference in the actual ADC value compared to the expected ADC value or due to a difference in the actual reference voltage compared to the expected reference voltage value), the computing device 100/202 may prompt a termination of the control circuit 250A as has been described herein.

Figure 5:
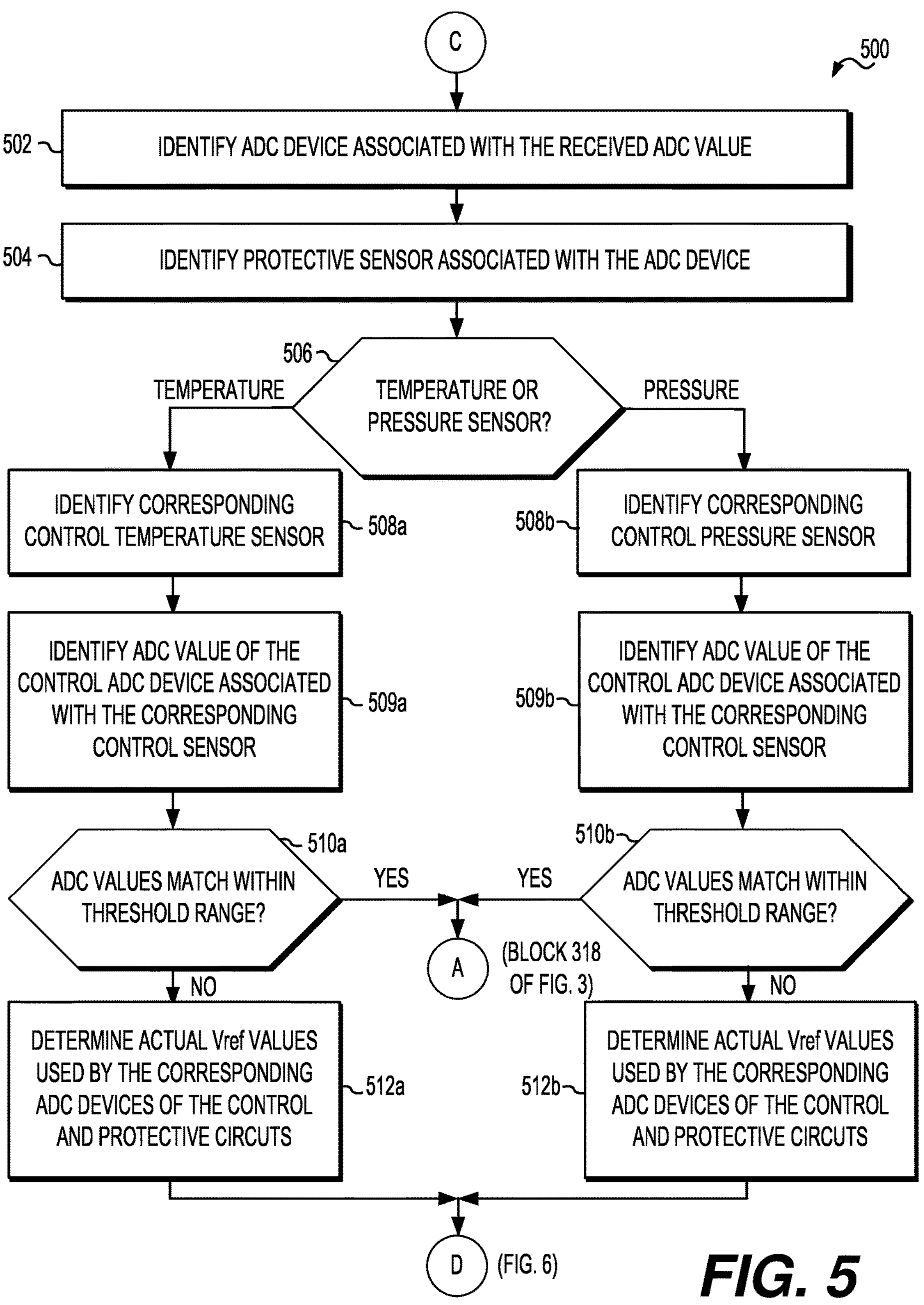
FIG. 5 is a process flow diagram of an example process for verifying voltage and ADC measurements obtained by a protective circuit of a medical fluid treatment system, according to an example embodiment of the present disclosure.

FIG. 5 is a process flow diagram of an example process 500 for verifying voltage and ADC measurements obtained by a protective circuit of a medical fluid treatment system, according to an example embodiment of the present disclosure. As previously discussed, process 500 may be performed by the computing device 100/202 during the pretreatment test after the computing device 100/202 has received an ADC value from the control circuit (e.g., if block 320 of FIG. 3 is true). In some embodiments, one or more step or method discussed in process 500 may be substantively similar to one or more step or method of process 400. Further, in some aspects, one or more step or method of processes 400 and 500 may be performed in parallel and/or combined (e.g., blocks 408A through 412A and 508A through 512A, and/or blocks 408B through 412B and blocks 508B through 512B).

Referring to process 500, the computing device 100/202 may identify the ADC device 215B associated with the received ADC value (block 502), and may identify the protective sensor 212B/214B associated with the identified ADC device 215B (block 504). At block 506, the computing device 100/202 may identify whether the protective sensor 212B/214B is a temperature sensor 214B or a pressure sensor 212B.

If the protective sensor is a temperature sensor 214B (referred to herein as protective temperature sensor), the computing device 100/202 may identify a corresponding temperature sensor 214A in the control circuit 250A (referred to herein as control temperature sensor) (block 508A). The computing device 100/202 may identify the ADC device 215A associated with the corresponding control temperature sensor 214A (referred to herein as the control ADC device associated with the control pressure sensor), and may determine the corresponding ADC value received from that control ADC device 215A (block 509A).

At block 510A, the computing device 100/202 may determine whether the ADC values match within a threshold range. The ADC values being compared at bock 510A are the ADC value received from the ADC device 215B of the protective circuit 250B (e.g., at block 320) and the ADC value received from the corresponding control ADC device 215A of the control circuit 250A. The threshold range may be a predetermined tolerance level to identify whether the two ADC values satisfy a similarity or matching threshold. The threshold range may be adjusted, e.g., by an operator of the medical fluid treatment system 10. If there is a match, the computing device 100/202 may deem that the ADC devices (protective ADC device 215B and the control ADC device 215A), from which the ADC values are received, are not defective. The computing device 100/202 may continue to monitor to see if there are ADC values received from the control and protective circuits 250A, 250B (e.g., by proceeding to block 318 as previously described in relation to FIG. 3). Also or alternatively, the computing device 100/202 may deem, based on the match, that the two ADC devices (the protective ADC device 215B of the protective temperature sensor 214B and the control ADC device 215A of the corresponding control temperature sensor 214A) perform similarly enough. For example, it may be possible that any defect in one of the two ADC devices is countered by a defect to the same degree in the other of the two ADC devices, thus negating the detrimental effect of the defect. As will be described further in connection with FIG. 6, the computing device 100/202 may compare the ADC value outputted by its shared voltage rails (e.g., 3.3V and 5V) with the ADC values from the control and/or protective circuits 250A, 250B. By using a third ADC value (e.g., from the shared voltage rail surrounding the computing device 100/202 itself), an additional layer of check may be provided to confirm that the ADC values are reasonable.

If, at block 510A, the ADC values do not match, the computing device 100/202 may determine the actual reference voltage values used by the corresponding ADC devices of the protective and control circuits 250A, 250B. As explained previously, the relationship between reference voltage, input voltage, ADC value, and a resolution of an ADC device may be summarized as:

$$Vin = ADC\frac{Vref}{2^n},$$

where Vin is the input voltage received by the ADC device (from its associated sensor), ADC is the ADC value outputted by the ADC device, Vref is the reference voltage associated with the sensor, and $2^n$ refers to the number of discrete values the ADC is configured to output (e.g., a resolution of the ADC device). Since the resolution ($2^n$) of the ADC device is determined in block 308, the expected input voltage is estimated based on pretreatment conditions in block 312, and the ADC value (ADC) received from the protective ADC device in block 320, the actual reference voltage ($Vref_{actual}$) may be computed as:

$$Vref_{actual} = 2^n \frac{Vin}{ADC}.$$

Moreover, the actual reference voltage of an ADC device may be different from the expected reference voltage value of the ADC device that is computed in block 316. For example, a defective ADC device may yield an actual reference voltage that is different from the expected reference voltage. Thus, at block 512A, the computing device 100/202 determines the actual reference voltage values used by the ADC devices associated with the corresponding temperature sensors of the protective and control circuits 250A, 250B (ADC device 215B associated with the protective temperature sensor 214B and the ADC device 215A associated with the control temperature sensor 214A).

Process 500 may proceed to process 600 shown in FIG. 6 (as indicated by label "D" in FIGS. 5 and 6. As will be described further below, in process 600, the computing device 100/202 may use the actual ADC values and actual reference voltage values to determine which ADC device, the control ADC device 215A or the protective ADC device 215B, is at fault.

If, at block 506, the computing device 100/202 determines that the protective sensor associated with the ADC device is a pressure sensor 212B (protective pressure sensor 212B), the computing device 100/202 may proceed through blocks 508B, 509B, 510B, and 512B, which may share one or more steps or methods as the previously discussed blocks 508A, 509A, 510A, and 512A.

For example, the computing device 100/202 may identify a corresponding pressure sensor 212A in the control circuit 250A (referred to herein as control pressure sensor) (block 508B). The computing device 100/202 may identify the ADC device 215A associated with the corresponding control pressure sensor 212A (referred to herein as the control ADC device associated with the control pressure sensor 212A), and may determine the corresponding ADC value received from that control ADC device 215A (block 509B).

At block 510B, the computing device 100/202 may determine whether the ADC values match within a threshold range. The ADC values being compared at block 510B are the ADC value received from the ADC device 215B of the protective circuit 250B (e.g., from block 320) and the ADC value received from the corresponding control ADC device 215A of the control circuit 250A. The threshold range may be a predetermined tolerance level to identify whether the two ADC values satisfy a similarity or matching threshold. The threshold range may be adjusted, e.g., by an operator of the medical fluid treatment system 10. If there is a match, the computing device 100/202 may deem that the ADC devices (protective ADC device 215B associated with the protective pressure sensor 212B and the control ADC device 215A associated with the corresponding control pressure sensor 212A), from which the ADC values are received, are not defective. Also or alternatively, the computing device 100/202 may deem, based on the match, that the two ADC devices (215A and 215B) perform similarly enough. In such cases, it may be possible, for example, that any defect in one of the two ADC devices is countered by a defect to the same degree in the other of the two ADC devices, thus negating the detrimental effect of the defect. If there is a match, the computing device 100/202 may continue monitoring to see if there are ADC values received from the control and protective circuits 250A, 250B (e.g., by proceeding to block 318 of FIG. 3). As will be described further in connection with FIG. 6, the computing device 100/202 may compare the ADC value outputted by its shared voltage rails (e.g., 3.3V and 5V) with the ADC values from the control and/or protective circuits 250A, 250B. By using a third ADC value (e.g., from the computing device 100/202 itself), an additional layer of check may be provided to confirm that the ADC values are reasonable.

If, at block 510B, the ADC values do not match, the computing device 100/202 may determine the actual reference voltage values used by the corresponding ADC devices of the protective and control circuits (250B and 250A, respectively). As explained previously, the relationship between reference voltage, input voltage, ADC value, and a resolution of an ADC device may be summarized as:

$$Vin = ADC\frac{Vref}{2^n},$$

where Vin is the input voltage received by the ADC device (from its associated sensor), ADC is the ADC value outputted by the ADC device, Vref is the reference voltage associated with the sensor, and $2^n$ refers to the number of discrete values the ADC is configured to output (e.g., a resolution of the ADC device). Since the resolution ($2^n$) of the ADC device is determined in block 308, the expected input voltage is estimated based on pretreatment conditions in block 312, and the ADC value (ADC) is received from the protective ADC device in block 320, the actual reference voltage ($Vref_{actual}$) may be computed as:

$$Vref_{actual} = 2^n \frac{Vin}{ADC}.$$

Moreover, the actual reference voltage of an ADC device may be different from the expected reference voltage value of the ADC device that is computed in block 316. For example, a defective ADC device may yield an actual reference voltage that is different from the expected reference voltage. Thus, at block 512B, the computing device 100/202 determines the actual reference voltage values used by the ADC devices associated with the corresponding pressure sensors of the protective and control circuits (ADC device 215B associated with the protective pressure sensor 212B and the ADC device 215A associated with the control pressure sensor 212A).

Process 500 may proceed to process 600 shown in FIG. 6 (as indicated by label "D" in FIGS. 5 and 6. As will be described further below, in process 600, the computing device 100/202 may use the actual ADC values and actual reference voltage values to determine which ADC device, the protective ADC device 215B or the control ADC device 215A, is at fault. In some embodiments, if the computing device 100/202 determines that the protective circuit 250B is at fault as a result of the defective ADC device 215B (e.g., due to a difference in the actual ADC value compared to the expected ADC value or due to a difference in the actual reference voltage compared to the expected reference voltage value), the computing device 100/202 may generate a warning to the operator of the medical fluid treatment system 10 (e.g., to warn against using the protective circuit 250B if the control circuit 250A malfunctions).

FIG. 6 is a process flow diagram of an example process 600 for assessing fault, based on voltage and ADC measurements in a medical fluid treatment system 10, according to an example embodiment of the present disclosure. As previously discussed, process 600 may be performed by the computing device 100/202 after the computing device 100/202 has determined that there is an mismatch or inconsistency in ADC values received by ADC devices (215A and 215B) of corresponding pressure sensors (e.g., a mismatch between an ADC value received by a control ADC device associated with a control pressure sensor 212A and an ADC value received by a protective ADC device associated with a corresponding protective pressure sensor 212B) or a mismatch or inconsistency in ADC values received by ADC devices of corresponding temperature sensors (e.g., a mismatch between an ADC value received by a control ADC device associated with a control temperature sensor 214A and an ADC value received by a protective ADC device associated with a corresponding protective temperature sensor 214B). In some embodiments, process 600 may be performed even if there is a match in the ADC values received by corresponding ADC devices of (in the control and protective circuit) to address the possibility where both ADC devices are defective.

Process 600 may begin with the computing device 100/202 comparing the actual reference voltage value and the expected reference voltage value of a control ADC device 215A at issue (block 602). As previously discussed (e.g., in blocks 410A and 410B of process 400), the control ADC device 215A at issue is a control ADC device 215A associated with a control sensor 212A/214A, for which the ADC value outputted by the control ADC device 215A does not match (e.g., does not satisfy a similarity threshold) with an ADC value outputted by a protective ADC device 215B associated with a corresponding protective sensor 212B/214B. As previously discussed, the expected reference voltage value for the control ADC device 215A at issue is determined or received at block 316 of process 300 (e.g., based on known pretreatment conditions, and expected ranges for sensor output based on the known pretreatment conditions). As previously discussed, the actual reference voltage value for the control ADC device 215A at issue may be received or determined at blocks 412A and/or 412B of process 400.

The computing device 100/202 may determine whether the difference between the actual reference voltage value and the expected reference voltage value of the control ADC device 215A at issue is within a threshold range (e.g., thereby satisfying a similarity threshold and/or tolerance level) (block 604). The threshold range may be adjusted, e.g., by an operator of the medical fluid treatment system 10.

If the difference between the actual reference voltage value and the expected reference voltage value is large enough (e.g., is not within the threshold range), the computing device 100/202 may register an error for the control circuit 250A (block 606). By registering the error, the computing device 100/202 may deem that the inconsistency between the ADC value of the control ADC device 215A and the corresponding protective ADC device 215B is due to a defect of the control ADC device 215A, as determined through a difference in the expected reference voltage value and the actual reference voltage value used by the control ADC device 215A. Since the control ADC device 215A is part of the control circuit 250A, and ADC values outputted by the control ADC device 215A may typically be used to control various crucial components or functions of the medical fluid treatment system 10, the control circuit 250A may be deemed as defective. In some embodiments, error may be registered for one or more component of the control circuit 250A, for example, where the remaining components of the control circuit 250A may function normally and may compensate for the defective components. In such embodiments, the defective control ADC device 215A and one or more of the associated sensor and nearby valves or pumps may be registered as having errors, instead of, or in addition to, the entirety of the control circuit 250A.

Afterwards, or if the difference at block 604 satisfies the threshold range, the computing device 100/202 may compare, the actual reference voltage value and the expected reference voltage value of a protective ADC device at issue (block 608). As previously discussed (e.g., in blocks 510A and MOB of process 500), the protective ADC device at issue is a protective ADC device 215B associated with a protective sensor 212B/214B, for which the ADC value outputted by the protective ADC device 215B does not match (e.g., does not satisfy a similarity threshold) with an ADC value outputted by a control ADC device 215A associated with a corresponding control sensor 212A/214A. As previously discussed, the expected reference voltage value for the protective ADC device 215B at issue is determined or received at block 316 of process 300 (e.g., based on known pretreatment conditions, and expected ranges for sensor output based on the known pretreatment conditions). As previously discussed, the actual reference voltage value for the protective ADC device 215B at issue may be received or determined at blocks 512A and/or 512B of process 500.

The computing device 100/202 may determine whether the difference between the actual reference voltage value and the expected reference voltage value of the protective ADC device 215B at issue is within a threshold range (e.g., thereby satisfying a similarity threshold and/or tolerance level) (block 610). The threshold range may be adjusted, e.g., by an operator of the medical fluid treatment system 10.

If the difference between the actual reference voltage value and the expected reference voltage value is large enough (e.g., the difference is not within the threshold range), the computing device 100/202 may register an error for the protective circuit 250B (block 612). By registering the error, the computing device 100/202 may deem that the inconsistency between the ADC value of the protective ADC device 215B and the corresponding control ADC device 215A is due to a defect of the protective ADC device 215B, as determined from the significant difference in the expected reference voltage value and the actual reference voltage value used by the protective ADC device 215B. Since the protective ADC device 215B is part of the protective circuit 250B, and since ADC values outputted by the protective ADC device 215B are typically used to control various crucial components or functions of the medical fluid treatment system 10 (e.g., in the event that the control circuit 250A is deactivated, not functioning correctly, and/or defective), a defective protective ADC device 215B may result in the protective circuit 250B to be deemed as defective. In some embodiments, error may be registered for one or more component of the protective circuit 250B, for example, if remaining components of the protective circuit 250B may function normally and can compensate for the defective components. In such embodiments, the defective protective ADC device 215B and one or more of the associated sensor and nearby valves or pumps may be registered as having errors, instead of, or in addition to, the entirety of the protective circuit 250B.

In some embodiments, the computing device 100/202 may compare an estimated input voltage value and an actual (e.g., calculated) input voltage value of an ADC device at issue (e.g., in either the control or protective circuits). For example, the computing device 100/202 may determine, for the ADC device 215A/215B at issue, based on its expected reference voltage value and the identified resolution of the ADC device ($2^n$), an expected input voltage value provided to the ADC device 215A/215B at issue by its associated sensor. As previously discussed the expected reference voltage may be based on a known pretreatment condition. The computing device 100/202 may also determine, for the ADC device 215A/215B at issue, based on the actual reference voltage value of the ADC device 215A/215B at issue, an estimated input voltage value received by the ADC device 215A/215B at issue. As is to be appreciated, the galvanic isolation may prevent a direct measuring of the actual input voltage so the input voltage may be estimated as $$Vin = ADC\frac{Vref}{2^n}.$$

If an error is registered for both the control circuit 250A and the protective circuit 250B, the computing device 100/202 may determine whether the registered error for the control circuit 250A is greater than the registered error for the protective circuit 250B (block 614). The magnitude of an error may be determined based on one or more factor, including but not limited to: a magnitude of the difference between the an actual reference voltage used by an ADC device 215A/215B at issue and the expected reference voltage that the ADC device would have used (e.g., during normal and/or non-defective conditions); a number of ADC devices 215A/215B at issue for a given circuit; a significance of an ADC device (e.g., marked by the level of control it exerts in the medical fluid treatment system); or a combination thereof. If the registered error for the control circuit 250A is greater than the registered error for the protective circuit 250B, the computing device 100/202 may terminate (e.g., disable) the control circuit 250A (block 624). Also or alternatively, a warning may be generated indicating that the control circuit 250A is defective. In some aspects, the termination of the control circuit 250A may cause the activation of the protective circuit 250B (e.g., if the protective circuit 250B does not have a registered error that exceeds a predetermined threshold), in order to continue medical fluid treatment to a patient but now via the protective circuit 250B. If the registered error for the control circuit 250A is not greater than the registered error for the protective circuit 250B (e.g., the registered error for the protective circuit 250B is greater than the registered error for the control circuit 250A), the computing device 100/202 may terminate (e.g., disable) or generate a warning regarding the use of the protective circuit 250B (block 616). For example, if the medical fluid treatment system 10 is currently using the control circuit 250A to provide treatment to a patient, an operator (e.g., a medical personnel) may be warned (e.g., via a display indicator) that the protective circuit 250B has an error. Thus, the operator may be warned against relying on the protective circuit 250B if the control circuit 250A were to fail. In some embodiments, if any of the control or protective circuit is deemed to be defective, the entire medical fluid treatment process of system 200 may stop, since the system 200 is intended to be single point safe.

In some aspects, it may be possible for a circuit to be defective even if there is no difference or insignificant difference (e.g., difference is within the threshold difference) between the actual reference voltage and the expected reference voltage of an ADC device for that circuit. In some embodiments, the control circuit 250A may share one or more voltage rail (e.g., a 3.3V and a 5.5 rail) with the computing device (e.g., the control unit 100 and/or CPU 202). For example, as previously shown in FIG. 2, a 3.3 V and a 5 V rail may supply power to both CPU 202 and the control circuit 250A. Such common rails (referred to as preset rails) may be used to determine if a control circuit 250A is at fault (e.g., in the event that the difference between the actual reference voltage and the expected reference voltage of a control ADC device is within a minimal range).

For example, at block 618, the computing device 100/202 may receive a local ADC value from the preset voltage rails (e.g., the 3.3 V and 5 V voltage rail supplying power to both the control circuit and the computing device). The local ADC value may be generated by an ADC device near the computing device (e.g., near CPU 202). Such ADC device may thus be "local" to the computing device, and is therefore on neither the control circuit nor the protective circuit. Thus, the ADC value outputted by the local ADC device may be referred to as local ADC value.

Further, at block 620, the computing device 100/202 may receive a control ADC value from the control ADC device at issue from the preset voltage rail (e.g., the 3.3 V and 5 V voltage rail supplying power to both the control circuit and the computing device). Since the local ADC device and the control ADC device are being supplied an input voltage from the same source, the preset voltage rails, the input voltage values for both ADC devices (e.g., the local ADC device and the control ADC device 215A) may be the same. Therefore, under normal circumstances, the output ADC values from both ADC devices should be similar (e.g., be within a threshold range).

Thus, at block 622, the computing device 100/202 may compare the ADC values output by each ADC device (the local ADC device and the control ADC device 215A) for the preset voltage rails to determine whether their difference is within a threshold range. As discussed, the threshold range (e.g., a similarity threshold and/or tolerance level) may be predetermined and/or may be adjusted, e.g., by an operator of the medical fluid treatment system 10.

If the difference in the ADC values between the control ADC device 215A and the local ADC device is not within the threshold range, the control circuit 250A may be deemed to be defective (e.g., on the basis of the control ADC device 215A at issue). At block 624, the computing device 100/202 may terminate (e.g., disable) the control circuit 250A. Also or alternatively, a warning may be generated indicating that the control circuit 250A is defective. In some aspects, the termination of the control circuit 250A may cause the activation of the protective circuit 250B (e.g., if the protective circuit 250B does not have a registered error), in order to continue medical fluid treatment to a patient.

If the difference in the ADC values between the control ADC device 215A and the local ADC device is within the threshold range, the computing device 100/202 may deem the control circuit 250 to be operating normally (e.g., non-defectively). Thus, the computing device 100/202 may continue and/or cause the control circuit 250A to continue normal operations of the medical fluid treatment system 10 (block 626).

Peritoneal Dialysis Fluid Supply Line Connection for Disinfection

Figure 7:
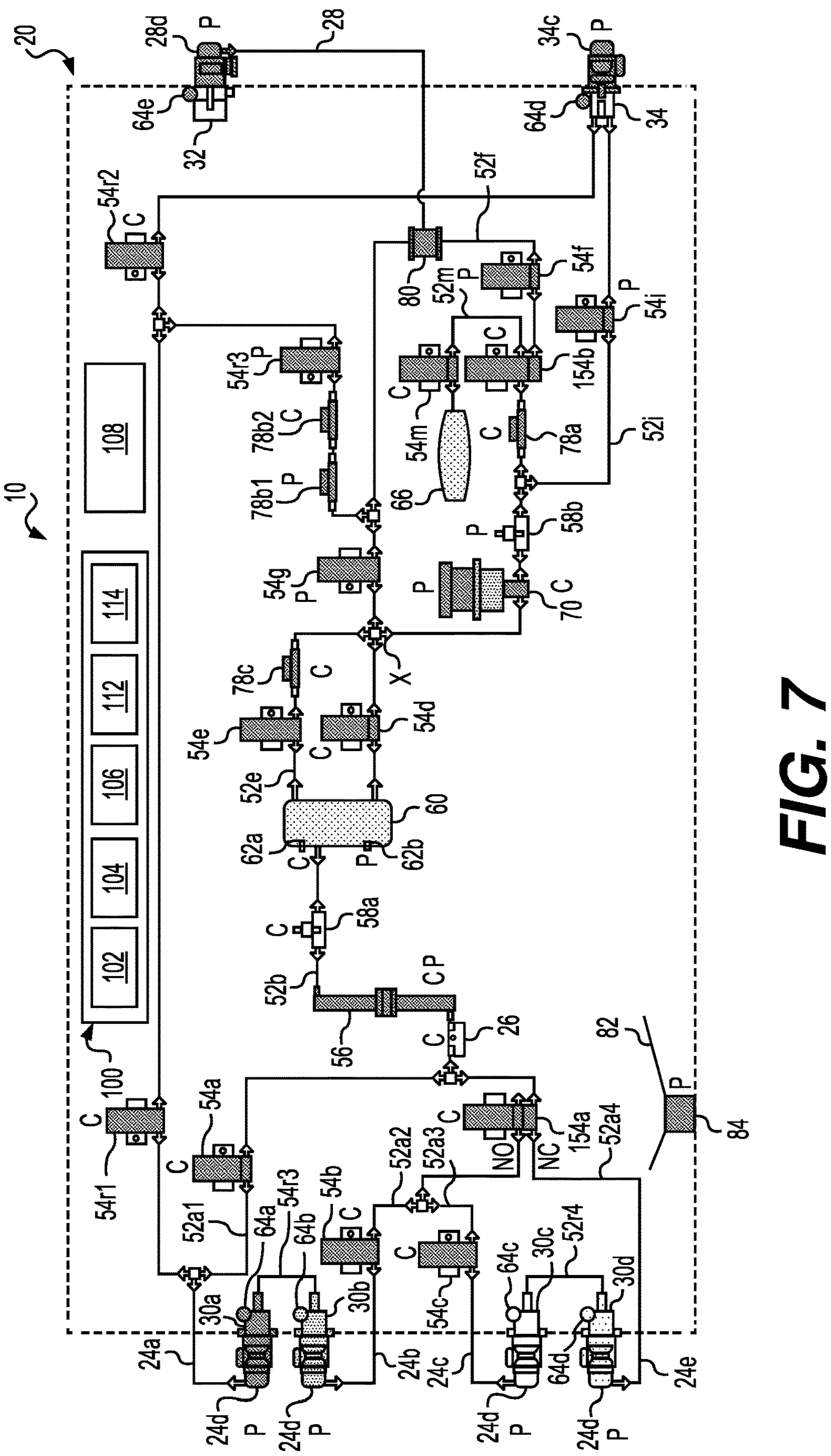
FIG. 7 is a schematic view of medical fluid system of FIG. 1 in a disinfection mode.

Referring now to FIG. 7, PD machine or cycler 20 of system 10 (FIG. 1) is illustrated in a disinfection mode. Here, treatment has ended and PD fluid containers or bags 38*a* to 38*d* have been removed. Distal ends 24*d* of flexible, reusable PD fluid lines 24*a* to 24*c* and 24*e* are removed from PD fluid containers or bags 38*a* to 38*d* and are connected instead to disinfection connectors 30*a* to 30*d*, respectively. Distal end 28*d* of flexible dual lumen reusable patient line 28 is removed from disposable filter set 40 after treatment and connected instead to patient line connector 32. Disposable drain line 36 is removed from drain line connector 34 and discarded. Cap 34*c* is closed against drain line connector 34. The flowpath of PD machine or cycler 20 is now closed and disinfection may proceed.

As illustrated in FIGS. 1 and 7, proximity sensors 64*a* to 64*f* are provided and output to control unit 100. Proximity sensors 64*a* to 64*f* may be any type of sensor capable of sensing the presence of something, e.g., hall effect sensors, other magnetic or electromagnetic sensors, ultrasonic sensors, inductive sensors, capacitive sensors and optical sensors. Proximity sensors 64*a* to 64*f* are positioned and arranged to ensure that each of disinfection connectors 30*a* to 30*d*, patient line connector 32 and drain line connector 34 are properly sealed to a mating connector for disinfection. Proximity sensors 64*a* to 64*d* are positioned and arranged to ensure that each of disinfection connectors 30*a* to 30*d*, respectively, are properly sealed distal end 24*d* distal end 24*d* of PD fluid lines for disinfection. Proximity sensors 64*e* and 64*f* are positioned and arranged to ensure that patient line connector 32 and drain line connector 34 are properly sealed to distal end 28*d* of reusable patient line 28 and by cap 34*c*, respectively, for disinfection.

As illustrated in FIGS. 1 and 7, proximity sensors 64*a* to 64*f* (labeled with P in FIG. 7) are part of the protective side of control unit 100. Prior to commencing disinfection, if the outputs of any of proximity sensors 64*a* to 64*f* sensors are not indicative of a properly sealed respective connector and associated flowpath, control unit 100 does not allow disinfection to proceed and in an embodiment provides an audio, visual or audiovisual message at user interface 108 to the patient or user to check the faulty one or more connection. If the connection can be fixed, as verified by the output from the previously fault sensing proximity sensor(s) 64*a* to 64*f*, then control unit 100 allows disinfection to proceed.

Figure 8:
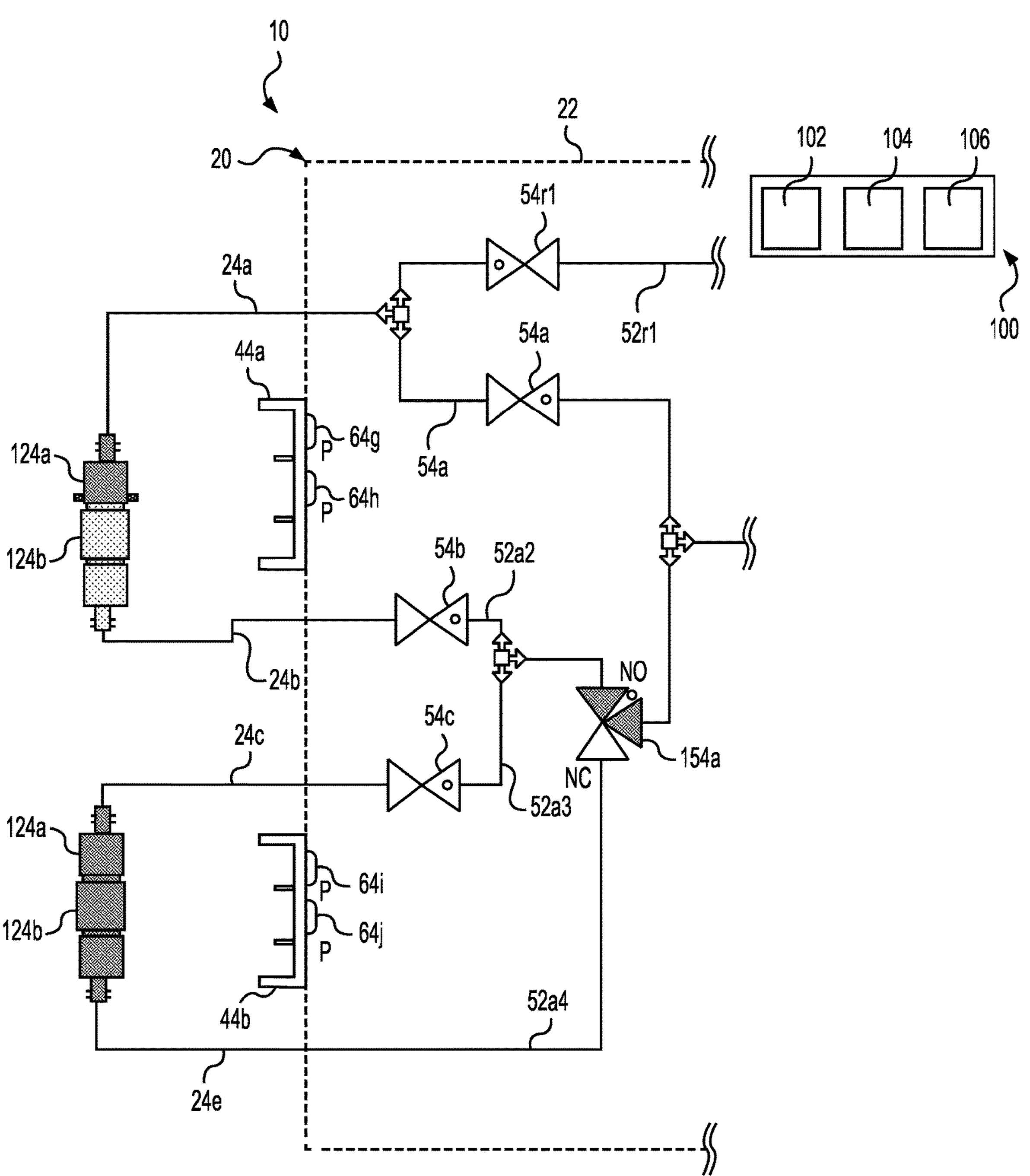
FIG. 8 a schematic view of an example embodiment of a medical fluid system having a streamlined and efficient structure for coupling peritoneal dialysis fluid supply lines together after treatment for disinfection.

Referring now to FIG. 8, an alternative embodiment for closing reusable PD fluid lines 24*a* to 24*c* and 24*e* for disinfection is illustrated. Here, disinfection connectors 30*a* to 30*d* and lines 52*r*3 and 52*r*4 leading to the disinfection connectors are eliminated. The fluid circuitry at the PD fluid container or bag end of PD machine or cycler 20 is simplified significantly. Still provided are supply valves Ma to Mc located along reusable internal lines 52*a*1 to 52*a*3, respectively. Three-way valve 154*a* communicating fluidly with flexible, reusable PD fluid line 24*e* via internal reusable line 52*a*4 is also provided.

In the illustrated embodiment, the ends of flexible, reusable PD fluid lines 24*a* and 24*c* are provided with a connector 124*a*, which is configured to mate sealingly with a connector 124*b* located at the ends of flexible, reusable PD fluid lines 24*b* and 24*e*. Mating connectors 124*a*, 124*b* may be threadingly mated, mated via a luer type connection or other suitable releasable and sealable connection that prevents heated, e.g., heated PD fluid, from leaking during disinfection. Another suit type of connector for mating connectors 124*a*, 124*b* includes a quick-connect connector that is pushed to make a sealed connection and is pulled back to release the connection. Because mating connectors 124*a*, 124*b* are reused over many treatments, they are made of a resilient material that tends not to scratch, chip or deform even over multiple, multiple treatment. Suitable materials include chemically and thermally stable plastics, e.g., polyphenylsulfone ("PPSU"), polyetheretherketone ("PEEK") or similar.

At the end of treatment, the patient or caregiver disconnects connector 124*a* from PD fluid container or bag 38*a*, disconnects connector 124*b* from PD fluid container or bag 38*b*, and connects connectors 124*a*, 124*b* together. The patient or caregiver also disconnects connector 124*a* from PD fluid container or bag 38*c*, disconnects connector 124*b* from PD fluid container or bag 38*d*, and connects connectors 124*a*, 124*b* together. The PD fluid bag or container side of PD machine or cycler 20 is now ready for disinfection.

In the above example, PD fluid container or bag 38*a* may be provided with a connector 124*b* or similar for being mated with connector 124*a* of flexible, reusable PD fluid line 24*a* for treatment. PD fluid container or bag 38*b* may be provided with a connector 124*a* or similar for being mated with connector 124*b* of flexible, reusable PD fluid line 24*b* for treatment. PD fluid container or bag 38*c* may be provided with a connector 124*b* or similar for being mated with connector 124*a* of flexible, reusable PD fluid line 24*c* for treatment. PD fluid container or bag 38*d* may be provided with a connector 124*a* or similar for being mated with connector 124*b* of flexible, reusable PD fluid line 24*e* for treatment.

In an alternative embodiment, each PD fluid container or bag 38*a* to 38*d* is provided with a "Y" or "T" type fitting having one leg leading to a connector 124*a* or similar and another leg leading to a connector 124*b* or similar. The unused connector 124*a*, 124*b* remains capped during treatment. Here, any PD fluid container or bag 38*a* to 38*d* may be connected to any flexible, reusable PD fluid line 24*a*, 24*b*, 24*c* or 24*e*.

As discussed above, disinfection connectors 30*a* to 30*d* are not provided in the embodiment of system 10 of FIG. 8. Likewise, machine-based proximity, e.g., hall effect, sensors 64*a* to 64*d* are not provided and are therefore not available to ensure, as part of the protective side of control unit 100, that the PD fluid bag or container side of PD machine or cycler 20 is ready for disinfection.

It is contemplated to check the connection of reusable PD fluid line connectors 124*a*, 124*b* in a number of ways as a condition for control unit 100 to allow disinfection to begin or continue. One way is for control unit 100 to perform a pressure or pressure decay test. In one example, control unit 100 causes valves Mg, 54*r*3 and 54*r*1 to be open and for dialysis fluid pump 70 to be actuated to pressurize lines 52*c*, 52*r*1, 24*a* and 24*b* to a test pressure as measured by one or both of pressure sensors 78*b*1 and 78*b*2. If the pressure holds over a test duration, e.g., one to ten seconds, control unit 100 determines that the connection between flexible, reusable PD fluid lines 24*a* and 24*b* is good. Control unit 100 may then cause three-way valve 154*a* to toggle such that dialysis fluid pump 70 may be actuated to further pressurize lines 52*a*4, 24*e* and 24*c* to a test pressure as measured by one or both of pressure sensors 78*b*1 and 78*b*2. If the pressure holds over a test duration, e.g., one to ten seconds, control unit 100 determines that the connection between flexible, reusable PD fluid lines 24*c* and 24*e* is good.

If both sets of connections between connectors 124*a*, 124*b* are good, control unit 100 proceeds to the next disinfection step. If the output of one or more pressure sensor 78*b*1, 78*b*2 indicates more than an allowable amount of pressure drop, control unit 100 does not allow disinfection to proceed and in an embodiment provides an audio, visual or audiovisual message at user interface 108 to the patient or user to check the connections between PD fluid connectors 124*a*, 124*b*. If the connection can be fixed, as verified by the output from one or more pressure sensor 78*b*1, 78*b*2, then control unit 100 allows disinfection to proceed.

Another way to check the connection of reusable PD fluid line connectors 124*a*, 124*b* is illustrated in FIG. 8. Here PD machine housing 22 may be provided with connector clips 44*a*, 44*b*. After treatment, user interface 108 provides an audio, visual or audiovisual message to the patient or caregiver to remove PD fluid containers or bags 38*a* to 38*d* from flexible, reusable PD fluid lines 24*a*, 24*b*, 24*c* and 24*e*, make the two connections between connectors 124*a*, 124*b*, and to clip the mated connectors 124*a*, 124*b* one each into connector clips 44*a*, 44*b*. Protective side proximity, e.g., hall effect, sensors 64*g* to 64*j* (marked with a P) outputting to control unit 100 are provided, such that two sensors 64*g*, 64*h* reside at connector clip 44*a* and two sensors 64*i*, 64*j* reside at connector clip 44*b*. In the illustrated embodiment, proximity sensor 64*g* senses to detect the presence of connector 124*a* of PD fluid line 24*a*, proximity sensor 64*h* senses to detect the presence of connector 124*b* of PD fluid line 24*b*, proximity sensor 64*i* senses to detect the presence of connector 124*a* of PD fluid line 24*c*, and proximity sensor 64*j* senses to detect the presence of connector 124*b* of PD fluid line 24*e*.

If the output from each proximity sensor 64*g* to 64*j* indicates that a mated connection between connectors 124*a*, 124*b* is present, control unit 100 proceeds to the next disinfection step. If the output of one or more proximity sensor 64*g* to 64*j* indicates that one or both connector(s) 124*a*, 124*b* is/are not present, control unit 100 does not allow disinfection to proceed and in an embodiment provides an audio, visual or audiovisual message at user interface 108 to the patient or user to check the connections between PD fluid connectors 124*a*, 124*b* and to make sure the mated connectors are clipped into connector clips 44*a*, 44*b*. If the connection can be fixed, as verified by the output from proximity sensors 64*g* to 64*j*, then control unit 100 allows disinfection to proceed.

In an embodiment, the pressure or pressure decay check discussed above is performed after the check by proximity sensors 64*g* to 64*j* indicates that PD fluid connectors 124*a*, 124*b* are present. Here, the pressure or pressure decay check is performed to check that the connection between PD fluid connectors 124*a*, 124*b* is tight and not to check if a connection has been made at all, which could lead to a free flow of PD fluid situation.

Viewing FIG. 8, Another alternative or additional way to check the connections of reusable PD fluid line connectors 124*a*, 124*b* is to run, e.g., coextrude, a conductive wire along the outside of each of PD fluid lines 24*a*, 24*b*, 24*c* and 24*e*, have the conductive wires make electrical connections with electrical conductors located within corresponding PD fluid line connectors 124*a*, 124*b*, provide a first voltage source (e.g., low voltage) in electrical communication with the conductive wires of PD fluid lines 24*a*, 24*b*, and provide a second voltage source (e.g., low voltage) in electrical communication with the conductive wires of PD fluid lines 24*c*, 24*e*. The conductors located within PD fluid line connectors 124*a*, 124*b* are positioned and arranged to make an electrical connection with each other when the PD fluid line connectors 124*a*, 124*b* are properly fluidically connected. A current or resistance sensor outputting to control unit 100 is also provided in the electrical loop of each mated pair of PD fluid line connectors 124*a*, 124*b*. If either set PD fluid line connectors 124*a*, 124*b* is properly fluidically connected, the current sensor will sense a characteristic flow of current, or the resistance sensor will sense a low resistance, indicating the proper connection. If either set PD fluid line connectors 124*a*, 124*b* is not properly fluidically connected or not connected at all, the current sensor will sense no current or a low flow of current, or the resistance sensor will sense a high resistance, indicating the non-proper or missing connection. The electrical wire way of verifying fluid connections may be used in combination with any of the other connection checks described herein.

It should be understood that various changes and modifications to the presently preferred embodiments described herein will be apparent to those skilled in the art. It is therefore intended that such changes and modifications be covered by the appended claims. For example, while a local ADC device may be used to determine whether a control circuit is at fault after the control circuit and protective circuit produce inconsistent ADC values, the local ADC may also be used to determine whether a control circuit is at fault, independent of any comparison or involvement of the protective circuit. For example, blocks 618 through 624 may be performed by the computing device to routinely monitor the performance of the control circuit, without having to compare ADC or reference voltage values from the control circuit with ADC or reference voltage values from the protective circuit (e.g., for a pair comprising an control ADC device and a protective ADC device).

The invention is claimed as follows:

1. A system for verifying reference voltage and analog-to-digital converter ("ADC") values during medical fluid treatment, the system comprising:

a control circuit including a plurality of control ADC devices and a plurality of control sensors, wherein each control ADC device is associated with a respective control sensor and facilitates medical fluid treatment based on an input voltage from the respective control sensor;

a protective circuit including a plurality of protective ADC devices and a plurality of protective sensors, wherein each protective ADC device is associated with a respective protective sensor, wherein the control circuit and the protective circuit are galvanically isolated from one another;

one or more processor; and a memory storing instructions that, when executed by the one or more processor, cause the system to:

initiate a pretreatment for the system, wherein the pretreatment exposes the plurality of control sensors and the plurality of protective sensors to common pretreatment conditions;

receive, during the pretreatment, a plurality of control ADC values corresponding to the plurality of control ADC devices, and a plurality of protective ADC values corresponding to the plurality of protective ADC devices; and register, based on a comparison of a control ADC value with a protective ADC value, an error for one or both of the control circuit or the protective circuit.

2. The system of claim 1, further comprising:

a central processing unit ("CPU");

a first optoisolator communicatively coupling the CPU to the control circuit; and a second optoisolator communicatively coupling the CPU to the protective circuit, wherein the first and second optoisolators galvanically isolate the control circuit from the protective circuit.

3. The system of claim 1, wherein exposing the plurality of control sensors and the plurality of protective sensors to the common pretreatment conditions comprises exposing the plurality of control sensors and the plurality of protective sensors to a common temperature range or a common pressure range.

4. The system of claim 1, wherein the instructions, when executed, further cause the system to:

determine, for each of the plurality of control ADC devices, based on the common pretreatment conditions and an expected voltage range of a respective control sensor associated with a respective control ADC device, an expected control reference voltage value of the respective control ADC device; and determine, for each of the plurality of protective ADC devices, based on the common pretreatment conditions and an expected voltage range of a respective protective sensor associated with a respective protective ADC device, an expected protective reference voltage value of the respective protective ADC device.

5. The system of claim 4, wherein the instructions, when executed, further cause the system to:

determine, based on the plurality of control ADC values and a number of bits that the plurality of control ADC devices are configured to output, a plurality of actual control reference voltage values corresponding to the plurality of control ADC values; and determine, based on the plurality of protective ADC values and a number of bits that the plurality of protective ADC devices are configured to output, a plurality of actual protective reference voltage values corresponding to the plurality of protective ADC values.

6. The system of claim 5, wherein the registering of the error for one or both of the control circuit or the protective circuit is further based on one or more of:

a comparison of an expected control reference voltage value of a control ADC device and an actual control reference voltage value for the control ADC device; or a comparison of an expected protective reference voltage value of a protective ADC device and an actual protective reference voltage value for the protective ADC device.

7. The system of claim 5, wherein the instructions, when executed, further cause the system to:

determine, for each of the plurality of control ADC devices, based on the expected control reference voltage value of the respective control ADC device, an expected control input voltage value of a respective control sensor associated with the respective control ADC device;

determine, for each of the plurality of control ADC devices, based on an actual control reference voltage value of the respective control ADC device, an actual control input voltage value of the respective control sensor associated with the respective control ADC device;

determine, for each of the plurality of protective ADC devices, based on the expected protective reference voltage value of the respective protective ADC device, an expected protective input voltage value of a respective protective sensor associated with the respective protective ADC device; and determine, for each of the plurality of protective ADC devices, based on an actual protective reference voltage value of the respective protective ADC device, an actual protective input voltage value of the respective protective sensor associated with the respective protective ADC device, wherein the registering of the error for one or both of the control circuit or the protective circuit is further based on one or more of:

a comparison of an expected control input voltage value of a control ADC device and an actual control input voltage value for the control ADC device; or a comparison of an expected protective input voltage value of a protective ADC device and an actual protective input voltage value for the protective ADC device.

8. The system of claim 1, wherein the plurality of control sensors comprise one or more control temperature sensor and one or more control pressure sensor, and wherein the plurality of protective sensors comprises one or more protective temperature sensor and one or more protective pressure sensor.

9. The system of claim 1, further comprising:

a plurality of pumps; and a plurality of valves, wherein the plurality of pumps and the plurality of valves perform, based on the plurality of control ADC values or the plurality of protective ADC values, the medical fluid treatment.

10. The system of claim 9, wherein the instructions, when executed, further cause the system to:

determine a plurality of actual control reference voltage values corresponding to the plurality of control ADC values; and determine a plurality of actual protective reference voltage values corresponding to the plurality of protective ADC values, wherein each of the plurality of actual control reference voltage values and each of the plurality of actual protective reference voltage values, is associated with one or more of:

an actual control reference voltage value of a control temperature sensor and an actual protective reference voltage value of a protective temperature sensor, respectively; or an actual control reference voltage value of a control pressure sensor and an actual protective reference voltage value of a protective pressure sensor, respectively.

11. The system of claim 1, wherein the error is registered for the control circuit, and wherein the instructions, when executed, further cause the system to:

disable the control circuit from facilitating the medical fluid treatment.

12. A method for verifying reference voltage and analog-to-digital converter ("ADC") values during medical fluid treatment, the method comprising:

initiating, by a computing device having a processor, a pretreatment for a medical fluid treatment system including a control circuit having a plurality of control sensors and a protective circuit having a plurality of protective sensors, wherein the pretreatment exposes the plurality of control sensors and the plurality of protective sensors to common pretreatment conditions;

receiving, by the computing device, during the pretreatment, a plurality of control ADC values corresponding to a plurality of control ADC devices associated with the respective plurality of control sensors, and a plurality of protective ADC values corresponding to a plurality of protective ADC devices associated with the respective plurality of protective sensors; and registering, by the computing device and based on a comparison of a control ADC value with a protective ADC value, an error for one or both of the control circuit or the protective circuit.

13. The method of claim 12, wherein exposing the plurality of control sensors and the plurality of protective sensors to the common pretreatment conditions comprises exposing the plurality of control sensors and the plurality of protective sensors to a common temperature range or a common pressure range.

14. The method of claim 12, further comprising:

determining, for each of the plurality of control ADC devices, based on the common pretreatment conditions and an expected voltage range of a respective control sensor associated with a respective control ADC device, an expected control reference voltage value of the respective control ADC device; and determining, for each of the plurality of protective ADC devices, based on the common pretreatment conditions and an expected voltage range of a respective protective sensor associated with a respective protective ADC device, an expected protective reference voltage value of the respective protective ADC device.

15. The method of claim 14, further comprising:

determining, based on the plurality of control ADC values and a number of bits that the plurality of control ADC devices are configured to output, a plurality of actual control reference voltage values corresponding to the plurality of control ADC values; and determining, based on the plurality of protective ADC values and a number of bits that the plurality of protective ADC devices are configured to output, a plurality of actual protective reference voltage values corresponding to the plurality of protective ADC values.

16. The method of claim 15, wherein registering the error for one or both of the control circuit or the protective circuit is further based on one or more of:

a comparison of an expected control reference voltage value of a control ADC device and an actual control reference voltage value for the control ADC device; or a comparison of an expected protective reference voltage value of a protective ADC device and an actual protective reference voltage value for the protective ADC device.

17. The method of claim 12, wherein the plurality of control sensors comprise one or more control temperature sensor and one or more control pressure sensor, and wherein the plurality of protective sensors comprise one or more protective temperature sensor and one or more protective pressure sensor.

18. The method of claim 17, further comprising:

determining a plurality of actual control reference voltage values corresponding to the plurality of control ADC values; and determining a plurality of actual protective reference voltage values corresponding to the plurality of protective ADC values, wherein each of the plurality of actual control reference voltage values and each of the plurality of actual protective reference voltage values is associated with one or more of:

an actual control reference voltage value of a control temperature sensor and an actual protective reference voltage value of a protective temperature sensor, respectively; or an actual control reference voltage value of a control pressure sensor and an actual protective reference voltage value of a protective pressure sensor, respectively.

19. The method of claim 12, wherein the error is registered for the control circuit, and further comprising:

disabling the control circuit from facilitating the medical fluid treatment.

20. A non-transitory computer readable medium for use on a computer system containing computer-executable programming instructions for verifying voltage and analog-to-digital converter ("ADC") values during medical fluid treatment, the instructions comprising:

initiating a pretreatment for a medical fluid treatment system including a control circuit having a plurality of control sensors and a protective circuit having a plurality of protective sensors, wherein the pretreatment exposes the plurality of control sensors and the plurality of protective sensors to common pretreatment conditions;

receiving, during the pretreatment, a plurality of control ADC values corresponding to a plurality of control ADC devices associated with the respective plurality of control sensors, and a plurality of protective ADC values corresponding to a plurality of protective ADC devices associated with the respective plurality of protective sensors;

determining, based on the common pretreatment conditions, a plurality of actual control reference voltage values corresponding to the plurality of control ADC values, and a plurality of actual protective reference voltage values corresponding to the plurality of protective ADC values; and registering, based on an actual control reference voltage value or an actual protective reference voltage value, and based on a comparison of a control ADC value with a protective ADC value, an error for one or both of the control circuit or the protective circuit.

* * * * *